United States Patent [19]

Hulin

[11] Patent Number: 5,306,726
[45] Date of Patent: Apr. 26, 1994

[54] 3-ARYL-2-HYDROXYPROPIONIC ACID DERIVATIVES AND ANALOGS AS HYPOGLYCEMIC AGENTS

[75] Inventor: Bernard Hulin, Essex, Conn.

[73] Assignee: Pfizer Inc., New York, N.Y.

[21] Appl. No.: 980,404

[22] Filed: Nov. 24, 1992

Related U.S. Application Data

[60] Continuation-in-part and a division of PCT/US91/03858, May 31, 1991, which is a continuation-in-part of Ser. No. 537,673, Jan. 14, 1990, Pat. No. 5,089,514.

[51] Int. Cl.⁵ .......................................... C07D 263/56
[52] U.S. Cl. ..................................... 514/375; 548/217
[58] Field of Search ........................ 514/375; 548/217

[56] References Cited

U.S. PATENT DOCUMENTS

| | | | |
|---|---|---|---|
| 4,025,637 | 5/1977 | Dunwell | 514/375 |
| 4,340,605 | 7/1982 | Kawamatsu et al. | 548/183 |
| 4,703,052 | 10/1987 | Eggler et al. | 514/337 |
| 4,725,610 | 2/1988 | Meguro et al. | 514/369 |
| 4,753,956 | 6/1988 | Schnur | 514/375 |
| 4,775,687 | 10/1988 | Meguro | 548/190 |
| 4,897,393 | 1/1990 | Iijima et al. | 514/217 |
| 5,037,842 | 8/1991 | Goldstein | 514/375 |
| 5,158,964 | 10/1992 | Arrowsmith et al. | 514/375 |

FOREIGN PATENT DOCUMENTS

| | | |
|---|---|---|
| 0177353 | 4/1986 | European Pat. Off. |
| 0299620 | 1/1989 | European Pat. Off. |
| 8908650 | 9/1989 | PCT Int'l Appl. |
| 8908651 | 9/1989 | PCT Int'l Appl. |
| 8908652 | 9/1989 | PCT Int'l Appl. |
| 91-19702 | 12/1991 | PCT Int'l Appl. ................ 548/217 |

*Primary Examiner*—Donald G. Daus
*Attorney, Agent, or Firm*—Peter C. Richardson; Gregg C. Benson; Robert T. Ronau

[57] ABSTRACT

Certain 3-(phenyl, chroman-2-yl, benzofuran-5-yl or benzoxazol-5-yl)-2-(hydroxy or mercapto)propionic acid derivatives and analogs are useful as hypoglycemic and hypocholesterolemic agents.

4 Claims, No Drawings

3-ARYL-2-HYDROXYPROPIONIC ACID DERIVATIVES AND ANALOGS AS HYPOGLYCEMIC AGENTS

This is a continuation-in-part and a division of copending International application number PCT/US91/03858, entitled "3-Aryl-2-Hydroxypropionic Acid Derivatives and Analogs as Hypoglycemic Agents," filed May 31, 1991, which is a continuation-in-part of United States application Ser. No. 07/537,673, entitled "3-Aryl-2-Hydroxypropionic Acid Derivatives and Analogs as Hypoglycemic Agents", filed Jun. 14, 1990, now U.S. Pat. No. 5,089,514.

BACKGROUND OF THE INVENTION

The present invention relates to certain compounds of the formulas (I) and (II), depicted below, having utility as hypoglycemic and hypocholesterolemic agents, methods for their use and pharmaceutical compositions containing them.

In spite of the early discovery of insulin and its subsequent wide-spread use in the treatment of diabetes, and the later discovery and use of sulfonylureas (e.g. chlorpropamide, tolbutamide, acetohexamide, tolazamide) and biguanides (e.g. phenformin) as oral hypoglycemic agents, the treatment of diabetes remains less than satisfactory. The use of insulin, necessary in about 10% of diabetic patients in which synthetic hypoglycemic agents are not effective (Type I diabetes, insulin dependent diabetes mellitus), requires multiple daily doses, usually by self injection. Determination of the proper dosage of insulin requires frequent estimations of the sugar in the urine or in the blood. The administration of an excess dose of insulin causes hypoglycemia, with effects ranging from mild abnormalities in blood glucose or coma, or even death. Treatment of non-insulin dependent diabetes mellitus (Type II diabetes) usually consists of a combination of diet, exercise, oral agents, e.g., sulfonylureas, and in more severe cases, insulin. However, the clinically available hypoglycemics are unfortunately fraught with other toxic manifestations which limit their use. In any event, where one of these agents may fail in an individual case, another may succeed. A continuing need for hypoglycemic agents, which may be less toxic or succeed where others fail, is clearly evident.

Furthermore, atherosclerosis, a disease of the arteries, is recognized to be the leading cause of death in the United States and Western Europe. The pathological sequence leading to atherosclerosis and occlusive heart disease has been described in detail by Ross and Glomset in New England Journal of Medicine 295, 369–377 (1976). The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Cholesterol and cholesteryl ester account for most of this lipid. Further, it is postulated that most of the cholesterol found within the fatty streaks results from uptake from the plasma. These fatty streaks, in turn, give rise to development of the "fibrous plaque", which consists of accumulated intimal smooth muscle cells laden with lipid and surrounded by extra cellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the the arterial occlusion and tendency toward mural thrombosis and arterial muscular spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at high risk for development or progression of CVD because of this factor. Individuals who possess independent risk factors in addition to hyperlipidemia are at particularly high risk. Such independent risk factors include glucose intolerance, left ventricular hypertrophy hypertension, and being of the male sex. Cardiovascular disease is especially prevalent among diabetic subjects, at least in part because of the existence of multiple independent risk factors. Successful treatment of hyperlipidemia in the general population, and in diabetic subjects in particular, is therefore of exceptional medical importance.

The first step in recommended therapeutic regimens for hyperlipidemia is dietary intervention. While diet alone produces adequate response in some individuals, many others remain at high risk and must be treated further by pharmacological means. New drugs for the treatment of hyperlipidemia are, therefore, of great potential benefit for large numbers of individuals at high risk of developing CVD. Further, successful treatment of both the hyperlipidemia and hyperglycemia associated with the diabetic state with a single therapeutic agent is particularly desirable.

In addition to the hypoglycemic agents cited above, a variety of other compounds have been reported to possess this type of activity, as reviewed by Blank [Burger's Medicinal Chemistry, Fourth Edition, Part II, John Wiley and Sons, N.Y. (1979), pp. 1057–1080].

Schnur, in U.S. Pat. Nos. 4,342,771, 4,367,234 and 4,617,312, discloses various hypoglycemic oxazolidine-2,4-diones and thiazolidine-2,4-diones substituted at the 5-position with aryl or heteroaryl groups.

Kawamatsu et al., U.S. Pat. No. 4,340,605, disclose hypoglycemic thiazolidine-2,4-dione compounds of the formula

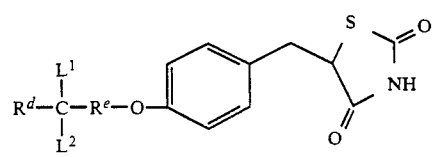

wherein $R^e$ is a bond or lower alkylene and when $R^d$ is an optionally substituted five- or six-membered heterocyclic group including one or two hetero-atoms selected from N, O, and S, $L^1$ and $L^2$ may each be defined as hydrogen. See also Sohda et al., Chem., Pharm. Bull. Japan, Vol. 30, pp. 3580–3600 (1982).

Eggler et al., U.S. Pat. No. 4,703,052, disclose hypoglycemic thiazolidinediones of the formula

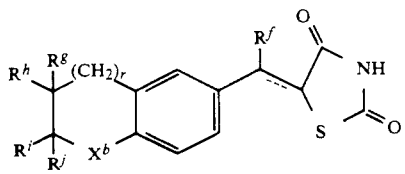

where the dotted line represents an optional bond, $R^f$ is H, methyl or ethyl, $X^b$ is O, S, SO, SO$_2$, CH$_2$, CO, CHOH or NR$^k$, R$^k$ is H or an acyl group and the numerous definitions of R$^g$, R$^h$, R$^i$ and R$^j$ include R$^g$, R$^h$ and R$^i$ as hydrogen or methyl and R$^j$ as optionally substituted phenyl, benzyl, phenethyl or styryl. EP 283,035A and EP 299,620A describe structurally related benzoxazole and benzofuran derivatives as antidiabetic agents.

Clark et al., in published World patent applications WO89/08650, WO89/8651 and WO89/08652 disclose hypoglycemic thiazolidinediones which collectively include compounds of the type:

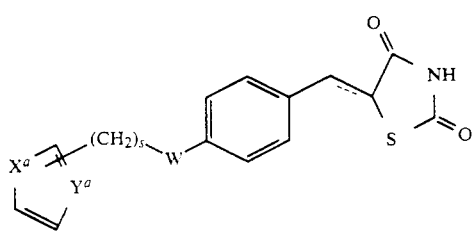

wherein ———— represents a bond or no bond; W is O, CO, CH$_2$, CHOH, or —CH=CH—; s is 0, 1 or 2; X$^a$ is S, O, NR$^a$, —CH=CH—, —CH=N— or —N=CH—; and Y$^a$ is CH or N.

SUMMARY OF THE INVENTION

The present invention is directed to compounds having the formulas

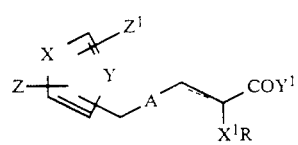
(I)

and

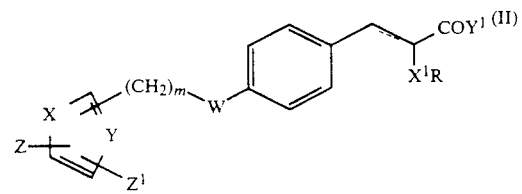
(II)

wherein
A is

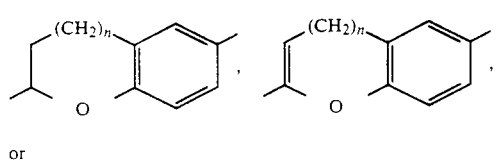
or

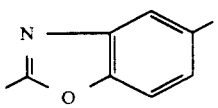

n is 0 or 1;
m is 0, 1 or 2;
———— represents a bond or no bond;
R is (C$_1$-C$_8$)alkyl, (C$_3$-C$_7$)cycloalkyl, (C$_3$-C$_8$)alkenyl, (C$_3$-C$_8$)alkynyl, phenyl, (C$_7$-C$_8$)phenylalkyl, (C$_2$-C$_8$)alkanoyl, or one of said groups mono- or disubstituted with (C$_1$-C$_3$)alkyl, trifluoromethyl, hydroxy, (C$_1$-C$_3$)alkoxy, fluoro or chloro;
W is O, CO, CH$_2$, CHOH or —CH=CH—;
X is S, O, NR$^2$, —CH=CH—, —CH=N— or —N=CH—;
R$^2$ is hydrogen, (C$_1$-C$_3$)alkyl, phenyl or benzyl;
Y is CH or N;
Z is H, amino, (C$_1$-C$_7$)alkyl, (C$_3$-C$_7$)cycloalkyl, phenyl, or phenyl mono- or disubstituted with (C$_1$-C$_3$)alkyl, trifluoromethyl, (C$_1$-C$_3$)alkoxy, phenyl, phenoxy, benzyl, benzyloxy, fluoro or chloro;
Z$^1$ is hydrogen or (C$_1$-C$_3$)alkyl;
X$^1$ is O, S, SO or SO$_2$; and
Y$^1$ is hydroxy, (C$_1$-C$_3$)alkoxy, phenoxy, benzyloxy, amino, (C$_1$-C$_4$)alkanoylamino, (C$_1$-C$_4$)alkanesulfonylamino, benzenesulfonylamino, naphthalenesulfonylamino, di[(C$_1$-C$_3$)alkyl]aminosulfonylamino, or one of said groups mono- or disubstituted with (C$_1$-C$_3$)alkyl, trifluoromethyl, hydroxy, (C$_1$-C$_3$)alkoxy, fluoro or chloro;
the pharmaceutically-acceptable cationic salts thereof when Y$^1$ is hydroxy; and
the pharmaceutically-acceptable acid addition salts thereof when the compound contains a basic nitrogen atom.

In the preferred compounds, the dotted line (————) represents no bond. The preferred values of A are

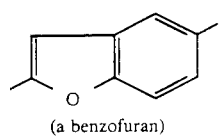
(a benzofuran)

or

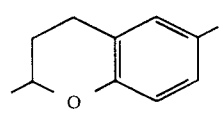
(a chroman or 3,4-dihydro-2H-1-benzopyran).

The preferred values of W are O or CO. In their preferred values, X, Y, Z and Z$^1$ are taken in such manner as to form a 5-methyl-2-phenyloxazol-4-yl group.

In those compounds in which ———— is not a bond, the carbon atom substituted by X$^1$R and COY$^1$ is asymmetric, such that these compounds can be either racemic or optically active. Resolution of a racemic form into a pair of optically active enantomers is exemplified below, and the present invention is not to be narrowly construed as limited to the racemic form of these compounds. Similarly, those compounds of the formula (I) wherein the group A contains a saturated ring possess an asymmetric carbon at position 2; and those compounds of the formula (II) contain an asymmetric carbon when W is CHOH.

The expression "pharmaceutically-acceptable cationic salts" is intended to define but not limited to such salts as the alkali metal salts, (e.g. sodium and potassium), alkaline earth metal salts (e.g. calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine) diethylamine, piperazine, tromethamine (2-amino-2-hydroxymethyl-1,3-propanediol) and procaine. An especially preferred such salt is the sodium salt.

The expression "pharmaceutically-acceptable acid addition salts" is intended to define but not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

Also embraced by the present invention are pharmaceutical compositions for use in treating a hyperglycemic mammal or a hypercholesterolemic mammal which comprises a blood glucose lowering amount or a blood cholesterol lowering amount of a compound of formula (I) or (II) and a pharmaceutically-acceptable carrier. The invention further comprises a method of lowering blood glucose in a hyperglycemic mammal which comprises administering to said mammal a blood glucose lowering effective amount of a compound of formula (I) or (II); and a method of lowering blood cholesterol in a hypercholesterolemic mammal which comprises administering to said mammal a blood cholesterol lowering amount of a compound of the formula (I) or (II).

DETAILED DESCRIPTION OF THE PRESENT INVENTION

The compounds of the formulas (I) and (II) of the present invention are readily prepared using conventional chemical processes. In the discussion which follows, the radical R' is defined as follows:

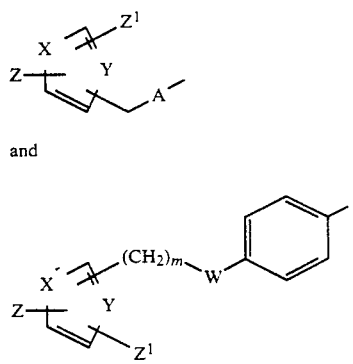

wherein m, A, W, X, Y, Z and $Z^1$ are as defined above.

When the dotted line (———) represents a bond, the compounds of the formula (I) or (II) wherein $Y^1$ is hydroxy and $X^1$ is S are generally prepared from the corresponding aldehyde by the two step sequence:

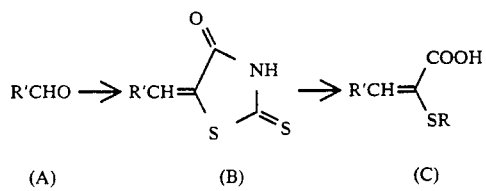

The first step of this sequence is accomplished by condensation of the aldehyde (A) with thiazolidine-4-one-2-thione (rhodanine) in the presence of a secondary amine such as piperidine or pyrrolidine in a reaction inert solvent such as ethanol at a temperature in the range of about 40°-100° C., conveniently at the reflux temperature of the reaction.

As used above and elsewhere herein, the expression "reaction inert solvent" refers to a solvent which does not interact with starting materials, reagents, intermediates or products in a manner which adversely affects the yield of the desired product.

When the dotted line (———) represents a bond, the compounds of the formula (I) or (II) wherein $X^1$ is O are generally prepared by condensation of the above aldehyde (A) with a suitably substituted acetic acid derivative, for example,

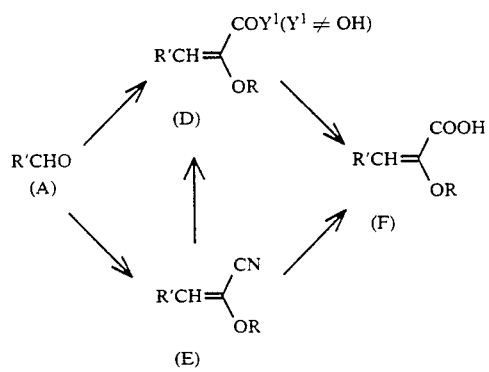

The condensation step is conveniently carried out by irreversibly converting the acrylic acid derivative, $CH_2=COR—CN$ or $CH_2=COR—COY^1$ (in which $Y^1$ is other than OH), to the sodium salt by the action of NaH in a reaction-inert solvent such as dimethylformamide, generally done at a temperature in the range of about 25°-60° C., and then adding the aldehyde and further reacting, generally at a somewhat higher temperature, e.g., 50°-100° C.

If the condensation product is an ester or an amide (D), it can, if desired, be conventionally hydrolyzed, preferably under aqueous basic conditions, to the acid. If the condensation product is a nitrile, it can be conventionally converted to ester, amide or acid, as desired. Specifically exemplified below is the conversion of nitrile to carboxamide, from which both of the expected (E) and (Z) isomers about the double bond are isolated.

The compounds (C) and (F) are further converted to compounds in which $Y^1$ is other than hydroxy by conventional transformations according to which acids are converted to esters, amides and imides. Furthermore, the double bond in such compounds can be conventionally reduced to form compounds of the formulas (I) and (II) wherein the dotted line (———) represents no bond. For example, reduction of the double bond is accomplished by conventional hydrogenation over a noble metal catalyst such as Pd/C, Rh/C or Rh(Ph₃P)₃Cl in a reaction inert solvent such as ethanol generally at temperatures in the range of ambient to 80° C., preferably at moderate pressures, e.g., up to about 125 psig so as not to require expensive and complex high pressure hydrogenation apparatus. However, the presently preferred routes to compounds of the formulas (I) and (II) wherein ———— represents no bond are as detailed below.

Compounds of the formulas (I) and (II) wherein the dotted line (————) represents no bond and $X^1$ is S are generally prepared from the corresponding amine via a two- or three-step reaction sequence:

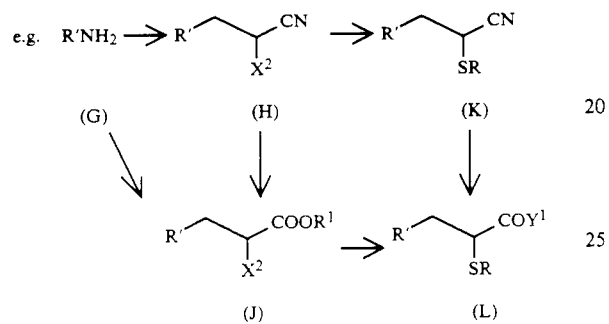

wherein R, R' and $Y^1$ are as defined above, $X^2$ is nucleophilically displacable group such as I, Cl, Br or $OSO_2CH_3$, and $R^1$ is an ester forming group such as $(C_1-C_3)$alkyl. According to this sequence, the amine (G) is first conventionally diazotized (e.g. with $NaNO_2$/conc.HBr or t-butyl nitrite) in the presence of a copper (II) salt and acrylonitrile or an acrylate ester to form the nitrile (H) or ester (J). This is followed by convention nucleophilic displacement of the group $X^2$ with $RS^-$, with or without conventional concurrent hydrolysis of the nitrile or ester. For example, an alpha-bromo ester (J, $X^2$=Br) is reacted with an excess of an alkali metal salt of a mercaptan or thiolcarboxylic acid (greater than two molar equivalents) in an aqueous solvent such as aqueous dimethylformamide, usually at an elevated temperature, e.g., in the range of 60°-100° C., to form the acid:

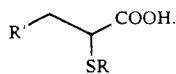

On the other hand, the nitrile or ester group is retained intact by reacting a compound (H) or (J) with a mercaptan or thiolcarboxylic acid in the presence of a base such as $K_2CO_3$ in an anhydrous reaction inert solvent such as dimethylformamide, generally at lower temperatures, e.g., in the range of about 15°-45° C. Prior to or after nucleophilic displacement, nitrile groups are converted to desired groups —$COY^1$ by conventional methods. For example, compounds wherein $Y^1$ is alkoxy are obtained by contacting the nitrile with dry HCl in an excess of the corresponding alkanol, a reaction usually carried out without additional solvent at a temperature in the range of about 15°-45° C.

Compounds of the formulas (I) and (II) wherein the dotted line (————) represents no bond and $X^1$ is O are generally prepared from the corresponding aldehyde according the following reaction sequences:

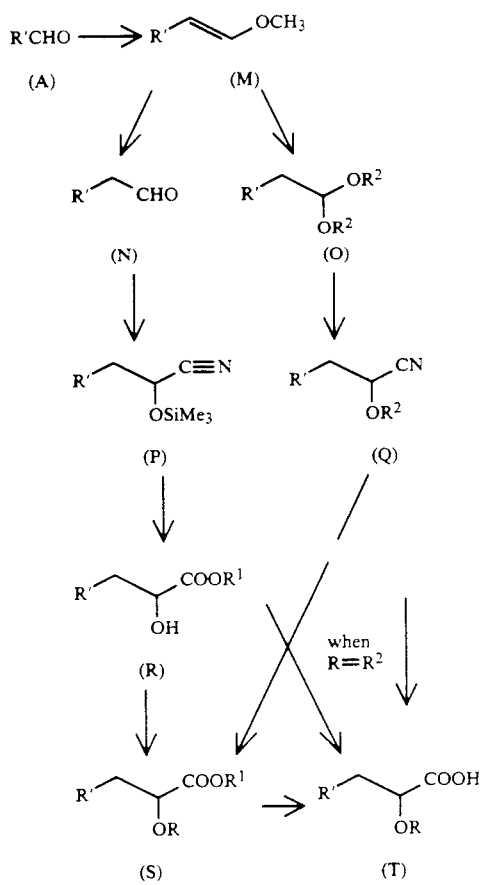

The enol ether (M) is conventionally formed from the aldehyde (A) via the Wittig reaction, using conditions as exemplified in specific examples below. In one further sequence, the enol ether is conventionally hydrolyzed with aqueous acid to form the aldehyde (N), which in turn is reacted with trimethylsilyl cyanide to form the O-trimethylcyanhydrin (P). The latter is conventionally reacted with an alcohol $R^1OH$ in the presence of anhydrous HCl to form the alpha-hydroxy ester (R). When RO is an ester, e.g., acetoxy, the hydroxyester (R) is readily converted to the ester by the action of the appropriate activated acid, e.g., an acid chloride or mixed anhydride, in the presence of at least one equivalent of a tertiary amine, usually in a reaction inert solvent such as tetrahydrofuran, conveniently at or near ambient temperature. When RO is an ether, e.g., ethoxy, the hydroxy ester (R) is reacted with NaH, under scrupulously anhydrous conditions in a reaction inert solvent such as tetrahydrofuran, so as to irreversibly form the sodium salt. The latter is then coupled with a mesylate ester or halide in typical nucleophilic displacement conditions described above, under the same anhydrous conditions to form the ester (S). Alternatively, under hydrous conditions (with at least one molar equivalent of water present), the latter reaction yields the acid (T). In a second further sequence, the enol ether (M) is reacted under anhydrous conditions with an alcohol $R^2OH$ in the presence of a strong anhydrous acid (e.g., p-toluenesulfonic acid) to form the acetal (O), which, upon reaction with trimethylsilyl cyanide, produces the cyanhydrin derivative (Q). The CN group in the latter compound is conventionally converted to the acid (T), e.g. by the action of NaOH in an aqueous solvent, or to the ester (S), e.g., by the action of dry HCl in an excess of an alcohol R$^1$OH.

Many of the compounds of the present invention are alternatively or preferably prepared from preformed compounds having different values of R, X$^1$ and Y$^1$. For example, sulfoxides (X$^1$=SO) are preferably formed from the corresponding sulfide (X$^1$=S) by the action of substantially one molar equivalent of a peroxyacid, conveniently, m-chloroperbenzoic acid. Sulfones (X$^1$=SO$_2$) are also obtained from the corresponding sulfide, but now generally with an excess (at least 2 molar equivalents) of the peracid. These oxidations are generally carried out in a reaction inert solvent such as tetrahydrofuran, at a temperature generally in the range of about 0°–40° C. Other transformations conveniently carried out to convert one preformed compound of the formula (I) or (II) to another such compound include esterification of acids, e.g.,

—COOH→—COCl→—COOR$^1$;

conversion of acids to amides or imides, e.g.,

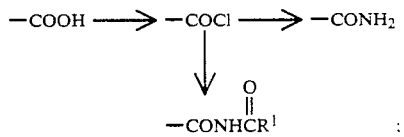

and ammonolysis of esters, e.g.,

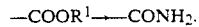
—COOR$^1$→—CONH$_2$.

Various of these transformations are exemplified below.

It will be readily understood by those skilled in the organic chemical art that in the compounds of the formulas (I) and (II) in which the dotted line (— — — —) represents no bond, the carbon atom bearing the X$^1$R and COY$^1$ groups is asymmetric and so potentially resolvable into a pair of optically active isomers. Substrates particularly well suited to such resolution are those carboxylic acids of the formulas (I) or (II) wherein Y$^1$ is OH, e.g., by combining the acid with an optically active amine, and separating the resulting pair of diastereomeric salts by fractional crystallization converting; or by reacting the acid with an optically alcohol or amine, and separating the resulting pair of diastereomeric esters or amides by chromatography or fractional crystallization, followed by hydrolysis of the separated isomers to yield the desired optically active acids. Such a resolution is exemplified below.

The pharmaceutically-acceptable cationic salts of the compounds of the present invention are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The acid addition salts of the compounds of the present invention are readily prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

The amines (R'NH$_2$) and aldehydes (R'CHO), when not commercially available or known in the prior art, are available by conventional synthetic methods, as exemplified below. For example the starting aldehydes are generally available as described in WO89/08650, WO89/8651 and WO89/08652 (cited above), and in U.S. Pat. No. 4,725,610; while the amino compounds are most generally available by reduction of the corresponding nitro compounds, as described in that same U.S. Pat. No. 4,725,610.

The present compounds of the formulas (I) and (II) are readily adapted to clinical use as hypoglycemic or hypocholesterolemic agents. The activity required for this former clinical use is defined by the test for hypoglycemic effect in ob/ob or db/db mice by the following procedure:

Five to eight week old C$_{57}$BL/6J-ob/ob or C57BL/K$_s$J-db/db mice (obtained from Jackson Laboratory, Bar Harbor, Me.) were housed five per cage under standard animal care practices. After a one week acclimation period, the animals were weighed and 25 microliters of blood was collected via an ocular bleed prior to any treatment. The blood sample was immediately diluted 1:5 with saline containing 2.5 mg/ml sodium fluoride and 2% sodium heparin, and held on ice for metabolite analysis. Animals were then dosed daily for five days with drug (5–50 mg/kg), a positive control (50 mg/kg) of ciglitazone; U.S. Pat. No. 4,467,902; Sohda et al., Chem. Pharm. Bull., vol. 32, pp. 4460–4465, 1984), or vehicle. All drugs were administered in a vehicle consisting of 0.25% w/v methyl cellulose. On day 5, the animals were weighed again and bled (via the ocular route) for blood metabolite levels. The freshly collected samples were centrifuged for two minutes at 10,000×g at room temperature. The supernatant was analyzed for glucose, for example, by the ABA 200 Bichromatic Analyzer TM, using the A-gent TM glucose UV reagent system* (hexokinase method) using 20, 60 and 100 mg/dl standards. Plasma glucose was then calculated by the equation, Plasma glucose (mg/dl) = Sample
value × 5 × 1.67 = 8.35 × Sample value where 5 is the dilution factor and 1.67 is the plasma hematocrit adjustment (assuming the hematocrit is 40%). TM A registered trademark of Abbott Laboratories, Diagnostics Division, 820 Mission Street, So. Pasadena, Calif. 91030.

*A modification of the method of Richterich and Dauwalder, Schweizerische Medizinische Wochenschrift, 101, 860 (1971).

The animals dosed with vehicle maintain substantially unchanged hyperglycemic glucose levels (e.g., 250 mg/dl), while positive control animals have depressed glucose levels (e.g., 130 mg/dl). Test compounds are reported in terms of % glucose normalization. For example, a glucose level which is the same as the positive control is reported as 100%.

Studies such as that described below demonstrate that the compounds of formula (I) effect the lowering of serum cholesterol levels in mammals.

Female mice (strain $C_{57}Br/cd$ J), obtained from Jackson Laboratories, Bar Harbor, Me., are used at age 8–12 weeks, following 2–4 weeks acclimation having free access to water and standard laboratory chow. Animals are divided randomly into three groups of 6–7 animals. All three groups are placed on a diet containing 0.75% cholesterol, 31% sucrose, 15.5% starch, 20% casein, 17% cellulose, 4.5% corn oil, 5% coconut oil, 0.25% cholic acid, 4% salts and 2% vitamin; permitted to feed ad lib for 18 days; and dose daily at 9–11 a.m. for the final 5 days by oral gavage, the control group with 5 ml/kg of vehicle (0.1% aqueous methyl cellulose) and the test groups with the compound under study at doses ranging from 0.1 to 10 mg/kg/day in vehicle. After the fourth day of dosing, the animals are fasted overnight, starting at 5 p.m. The following morning a fifth and final dose of the compound is administered to the test groups and, three hours later, the animals are sacrificed by decapitation. Blood from the body trunk is collected and allowed to clot, and the serum assayed enzymatically, using an Abbott VP automated analyzer, for HDL cholesterol, LDL and VLDL cholesterol, and total cholesterol. Whether judged on the basis LDL+VLDL cholesterol levels, total cholesterol levels or the ratio of LDL+VLDL/HDL, the compounds of this invention generally show favorable result in lowering cholesterol levels.

The present compounds of the formulas (I) and (II) are clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg/kg body weight of the subject per day, preferably about 0.10 to about 10 mg/kg body weight per day administered singly or as a divided dose. However, the optimum dosage for the individual subject being treated will be determined by the person responsible for treatment, generally smaller doses being administered initially and thereafter increments made to determine the most suitable dosage. This will vary-according to the particular compound employed and with the subject being treated.

The compounds can be used in pharmaceutical preparations containing the compound, or pharmaceutically acceptable acid salt thereof, in combination with a pharmaceutically-acceptable carrier or diluent. Suitable pharmaceutically-acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts of the compounds. The injectable solutions prepared in this manner can then be administered intravenously, intraperitoneally, subcutaneously, or intramuscularly, with intramuscular administration being preferred in man.

The present invention is illustrated by the following Examples. However, it should be understood that the invention is not limited to the specific details of these examples. Nomenclature used herein is based on Rigaudy and Klesney, IUPAC Nomenclature of Organic Chemistry, 1979 Ed., Pergammon Press, New York, 1979.

EXAMPLE 1

3-[4-(2-(5-Methyl-2-phenyl-4-oxazolyl)ethoxy)phenyl]-2-methylthio-2-propenoic Acid 4-[2-(5-Methyl-2-phenyl-4-oxazolyl)ethoxy]benzaldehyde (Takeda U.S. Pat. No. 4,725,610; 0.5 g, 1.6 mmol), rhodanine (0.21 g, 1.6 mmol) and piperidine (5 drops) were combined in ethanol (10 ml) and heated to reflux for 2 hours. The mixture was cooled and the precipitate filtered (0.35 g, mp 202.5°-203.5° C.). A slurry of this compound (0.25 g, 0.58 mmol) in 15% sodium hydroxide (5 ml) was heated to gentle reflux for 1 hour, then cooled and treated with a solution of methyl iodide (0.16 ml, 2.6 mmol) in methanol (5 ml). After 2 hours stirring at room temperature, the mixture was diluted with ice-water and acidified with 2N hydrochloric acid. The precipitate was filtered and recrystallized from 1:1 ethanol-water (10 ml) (0.11 g, mp 178.5°-182° C.).

Starting from the same aldehyde and using propyl iodide as the reagent, 3-[4-(2-(5-methyl-2-phenyl-4-oxazolyl)ethoxy)phenyl]-2-propylthio-2-propenoic acid was prepared by the same method (gummy solid).

$^1$H NMR (CDCl$_3$, 300 MHz) delta 0.91 (t, J=7.3Hz, 3H), 1.56 (tq, J=7Hz, 7Hz, 2H), 2.38 (s, 3H), 2.76 (t, J=7.3Hz, 2H), 3.01 (t, J=6.6Hz, 2H), 4.29 (t, J=6.6Hz, 2H), 6.92 (d, J=8.9Hz, 2H), 7.39-7.44 (m, 3H), 7.94-7.99 (m, 4H), 8.05 (s, 1H).

Starting from 4-[3-(5-methyl-2-phenyl-4-oxazolyl)-propionyl]benzaldehyde (WO89/08650), 3-[4-(3-(5-methyl2-phenyl-4-oxazolyl)propionyl)phenyl]-2-methylthio-2-propenoic acid was prepared by the same method (mp 150°-152° C.).

EXAMPLE 2

3-[4-(2-(5-Methyl-2-phenyl-4-oxazolyl)phenyl]-2-(methylthio)propanoic Acid

To a solution of 4-[2-(5-methyl-2-phenyl-4-oxazolyl)ethoxy]aniline (U.S. Pat. No. 4,725,610) (3.7 g, 12.6 mmol) in acetone (50 ml) and methanol (50 ml), cooled to 0° C., was added 48% hydrobromic acid (6.2 ml, 54 mmol), and after 5 minutes a solution of sodium nitrite (1.0 g, 15 mmol) in water (5 ml), dropwise, keeping the temperature below 5° C. After 15 minutes ethyl acrylate (8.6 ml, 79 mmol) was added dropwise, the mixture was warmed to 38° C. and cuprous oxide (0.42 g, 2.9 mmol) was added. The solution was stirred 1 hour at 40° C., then concentrated, diluted with aqueous ammonia and extracted with ethyl acetate (3×30 ml). The combined extracts were washed with water (2×), brine, dried over magnesium sulfate and concentrated. The product, ethyl alpha-bromo-4-[2-(5-methyl-2-phenyl-4-oxazolyl)ethoxy]benzenepropanoate, was isolated by flash chromatography (hexane/ethyl acetate, 4:1) as a yellow oil (1.17 g).

To a solution of ethyl alpha-bromo-4-[2-(5-methyl-2-phenyl-4-oxazolyl)ethoxy]benzenepropanoate (0.20 g, 0.44 mmol) in dimethylformamide (0.5 ml) was added a solution of sodium thiomethoxide (0.10 g, 1.4 mmol) in water (0.3 ml). The resulting solution was stirred at 80° C. for 16 hours. Water was added the mixture was acidified with 2N hydrochloric acid and extracted with ethyl acetate (2×). The combined extracts were washed with water (5×) and brine, dried over magnesium sulfate and concentrated to a yellow oil. The product was purified by flash-chromatography (hexane/ethyl aceate, 2:1) and obtained as a yellow gum (60 mg).

$^1$H NMR (CDCl$_3$, 300 MHz) delta 2.19 (s, 3H), 2.36 (s, 3H), 2.88 (dd, J=6Hz, 14Hz, 1H), 2.96 (t, J=7Hz, 2H), 3.16 (dd, J=9Hz, 14Hz, 1H), 3.41 (dd, J=6Hz, 9Hz, 1H), 4.13 (t, J=7Hz, 2H), 6.78 (d, J=8Hz, 2H), 7.11 (d, J=8Hz, 2H), 7.39-7.41 (m, 3H), 7.92-7.96 (m, 2H).

EXAMPLE 3

Ethyl 3-[4-(2-(5-Methyl-2-phenyl-4-oxazolyl)ethoxy)phenyl]-2-(acetylthio)propanoate To a solution of ethyl alpha-bromo-4-[2-(5-methyl-2-phenyl-4-oxazolyl)ethoxy]benzenepropanoate (0.18 g, 0.38 mmol) and thiolacetic acid (75 μl, 1.05 mmol) in dimethylformamide (2 ml) was added potassium carbonate (0.15 g, 1.05 mmol). After stirring overnight at room temperature, the mixture was poured into water and acidified with 1N hydrochloric acid, then extracted with ethyl acetate (3×). The combined extracts were washed with water (5×) and brine, dried over magnesium sulfate and concentrate to a yellow oil (0.11 g).

$^1$H NMR (CDCl$_3$, 300 MHz) delta 1.18 (t, J=7Hz, 3H), 2.31 (s, 3H), 2.37 (s, 3H), 2.91-2.99 (m, 1H), 2.97 (t, J=7Hz, 2H), 3.13 (dd, J=8Hz, 14Hz, 1H), 4.10 (q, J=7Hz, 2H), 4.21 (t, J=7Hz, 2H), 4.36 (dd, J=7Hz, 8Hz, 1H), 6.80 (d, J=8Hz, 2H), 7.09 (d, J=8Hz, 2H), 7.38-7.42 (m, 3H), 7.94-7.98 (m, 2H).

EXAMPLE 4

3-[2-((5-Methyl-2-phenyl-4-oxazolyl)methyl)-benzofuran-5-yl]-2-(propylthio)propanoate

A.

alpha-(5-Methyl-2-phenyl-4-oxazolyl)-5-nitro-2-benzofuranmethanol

A solution of 4-bromoacetyl-5-methyl-2-phenyloxazole (Takeda U.S. Pat. No. 4,725,610) (53 g, 0.19 mol), 5-nitrosalicyladehyde (32 g, 0.19 mol) and diisopropylethylamine (66 ml, 0.38 mol) in dimethylformamide (250 ml) was heated to 91°-94° C. for 3 hours. The mixture was cooled, diluted with ethyl acetate (300 ml) and the solid was collected. This solid was washed with chloroform (2×100 ml) and dried (56 g, mp 233°-234° C.). It was then placed in tetrahydrofuran (600 ml) and methanol (300 ml) and the slurry was cooled to 0° C. Sodium borohydride (9.1 g, 0.24 mol) was added portion-wise over 1 hour and the cloudy solution was stirred at 0° C. for 2 hours. The bulk of the solvent was removed in vacuo and water (700 ml) was added. The mixture was acidified with 6N hydrochloric acid and stirred for 30 minutes. The yellow-tan solid was collected, washed with water and dried (57 g, mp 166°-167° C).

B.

5-Amino-2-(5-methyl-2-phenyl-4-oxazolyl)methylbenzofuran alpha-(5-Methyl-2-phenyl-4-oxazolyl)-5-nitro-2-benzofuranmethanol (57 g, 0.16 mol) was dissolved in trifluoroacetic acid (350 ml), while cooling to 0° C. Triethylsilane (64 ml, 0.40 mol) was added. The solution was stirred 1.5 hours at 0° C. and overnight at room temperature. The solution was concentrated to near-dryness and the residue dissolved in ethyl acetate (750 ml). This solution was washed with water. The precipitate formed during the wash was collected. The organic solution was washed with satured sodium bicarbonate, during which more precipitate formed and was collected. The ethyl acetate phase of the filtrate was washed again with saturated sodium bicarbonate, then with brine, dried over sodium sulfate and concentrated. The residue was triturated with isopropyl ether and a solid was obtained. The combined solids obtained hereabove (51 g, 0.15 mol) were placed in a Parr bottle together with platinum oxide (3 g) and ethyl acetate (1.5 l) and hydrogenated at 40 psi for 1.25 hours. The catalyst was filtered through Celite, and after washing the filtering pad with more ethyl acetate, the solvent was removed in vacuo to give a yellow residue which was triturated with isopropyl ether (200 ml). The pale yellow solid was collected (37.1 g, mp 161.5°-162.5° C).

C.

alpha-Chloro-2-(5-methyl-2-phenyl-4-oxazolyl)methyl-5-benzofuranpropanenitrile

To a solution of acrylonitrile (11.2 ml, 0.17 mol) and tert-butyl nitrite (21.4 ml, 0.18 mmol) in acetonitrile (16 ml) was added cupric chloride (19.4 g, 0.14 mol), and 5-amino-2-(5-methyl-2-phenyl-4-oxazolyl)methylbenzofuran (37 g, 0.12 mol) portionwise over 40 minutes. The mixture was stirred for 30 minutes then poured into 20% hydrochloric acid (500 ml) and this solution was extracted with ethyl acetate (2×700 ml). The combined extracts were washed with 20% hydrochloric acid (2×250 ml), and brine (350 ml), dried over sodium sulfate and concentrated. The thick gum was extracted with boiling hexane (4×450 ml), the combined liquid phases were decanted, boiled down to ca. 1100 ml and cooled. The solid was collected (6.9 g). The mother liquor was concentrated and the residue was purified by flash-chromatography (hexanes/ethyl acetate, 4:1) to give a yellow solid which was combined with the material obtained from the hot hexane to give 16 g of the title compound as a yellow sticky solid.

D. Ethyl 3-[2-((5-Methyl-2-phenyl-4-oxazolyl)methyl)benzofuran-5-yl]-2-(propylthio)propanoate Hydrogen chloride was bubbled into a slurry of 2-(5-methyl-2-phenyl-4-oxazolyl)methyl-alpha-chloro-5-benzofuranpropanenitrile (16.3 g, 43 mmol) in 95% ethanol (600 ml) at 0° C. for 30 minutes, after which the mixture was stirred for 3 days at room temperature. The solvent was removed in vacuo and the residue partitioned between saturated sodium bicarbonate (350 ml) and ethyl acetate (500 ml). The aqueous layer was extracted with ethyl acetate (250 ml), the organic phases were combined, washed with brine, dried over sodium sulfate and concentrated. The oily residue was extracted with boiling hexane (2×400 ml), the solution was boiled down to 400 ml and cooled. The precipitated solid was collected. The filtrate was boiled down to 250 ml and allowed to cooled overnight and the solid was collected. The two solids were combined (11.5 g, mp 113°-115° C.).

To a solution of this solid (5 g, 12 mmol) in dimethylformamide (100 ml) was added propyl mercaptan (3.0 gml, 33 mmol), followed by potassium carbonate (4.6 g, 33 mmol). The slurry was stirred at room temperature overnight then poured into water (400 ml), acidified with 6N hydrochloric acid and extracted with ethyl acetate (2×300 ml). The combined extracts were washed with water (3×200 ml) and brine, dried over sodium sulfate and concentrated, leaving a yellow oil (4.3 g).

$^1$H NMR (CDCl$_3$, 300 MHz) delta 0.93 (t, J=7.5Hz, 3H), 1.15 (t, J=7.0 Hz, 3H), 1.56 (m, 2H), 2.32 (s, 3H), 2.57 (m, 2H), 2.99 (dd, J=6.4Hz, 13.9Hz, 1H), 3.22 (dd, J=9.4Hz, 13.6Hz, 1H), 3.48 (dd, J=6.4Hz, 9.1Hz, 1H), 3.99 (s, 2H), 4.08 (m, 2H), 6.40 (d, J=1.1Hz, 1H), 7.03 (dd, J=1.6Hz, 8.6Hz, 1H), 7.29 (s, 1H), 7.29 (d, J=7.8Hz, 1H), 7.37-7.42 (m, 3H), 7.96-7.99 (m, 2H).

Using the corresponding mercaptans, the following compounds were prepared by the same procedure:

Ethyl 3-[2-((5-methyl-2-phenyl-4-oxazolyl)methyl)-benzofuran-5-yl]-2-(phenylmethylthio)propanoate (oil)

$^1$H NMR (CDCl$_3$, 300 MHz) delta 1.20 (t, J=7Hz, 3H), 2.32 (s, 3H), 2.92 (dd, J=6Hz, 14Hz, 1H), 3.20 (dd, J=9Hz, 14Hz, 1H), 3.45 (dd, J=6Hz, 9Hz, 1H), 3.75 (d, J=13Hz, 1H), 3.80 (d, J=13Hz, 1H), 4.0 (s, 2H), 4.05 (m, 2H), 6.38 (s, 1H), 6.90 (dd, J=2Hz, 8Hz), 7.10-7.30 (m, 7H), 7.35-7.45 (m, 3H), 7.92-8.00 (m, 2H).

Ethyl 2-ethylthio-3-[2-((5-methyl-2-phenyl-4-oxazolyl)methyl)benzofuran-5-yl]propanoate (oil)

$^1$H NMR (CDCl$_3$, 300 MHz) delta 1.15 (t, J=7.4Hz, 3H), 1.20 (t, J=7.7Hz, 3H), 2.32 (s, 3H), 2.61 (dq, J=1.4Hz, 7.8Hz, 2H), 3.07 (dd, J=6.3Hz, 13.8Hz, 1H), 3.23 (dd, J=9.6Hz, 13.9Hz, 1H), 3.50 (dd, J=6.3Hz, 9.1Hz, 1H), 3.99 (s, 2H), 4.08 (m, 2H), 6.40 (s, 1H), 7.03 (dd, J=1.65Hz, 8.6Hz, 1H), 7.29 (s, 1H), 7.29 (d, J=8.3Hz, 1H), 7.37-7.42 (m, 3H), 7.42-7.99 (m, 2H).

Ethyl 3-[2-((5-methyl-2-phenyl-4-oxazolyl)methyl)-benzofuran-5-yl]-2-(phenylthio)propanoate (oil)

$^1$H NMR (CDCl$_3$, 300 MHz) delta 1.04 (t, J=7Hz, 3H), 2.32 (s, 3H), 3.08 (dd, J=6Hz, 14Hz, 1H), 3.22 (dd, J=9Hz, 14Hz, 1H), 3.88 (dd, J=6Hz, 9Hz, 1H), 3.95 (m, 2H), 4.00 (s, 3H), 6.38 (s, 1H), 7.00 (d, J=8Hz, 1H), 7.21-7.30 (m, 6H), 7.35-7.45 (m, 4H), 7.92-7.99 (m, 2H).

Ethyl -3-[2-((5-methyl-2-phenyl-4-oxazolyl)methyl)-benzofuran-5-yl]-2-(octylthio)propanoate (oil)

$^1$H NMR (CDCl$_3$, 300 MHz) delta 0.85 (t, J=6.5Hz, 3H), 1.18 (t, J=7.0Hz, 3H), 1.22-1.35 (m, 10H), 1.47-1.58 (m, 2H), 2.33 (s, 3H), 2.58 (m, 2H), 2.99 (dd, J=6.3Hz, 13.8Hz, 1H), 3.22 (dd, J=9.2Hz, 13.8Hz, 1H), 3.48 (dd, J=6.3Hz, 9.2Hz, 1H), 3.99 (s, 2H), 4.08 (m, 2H), 6.40 (s, 1H), 7.03 (dd, J=1.8Hz, 8.5Hz, 1H), 7.28 (s, 1H), 7.29 (d, J=7.9Hz, 1H), 7.37-7.42 (m, 3H), 7.95-7.99 (m, 2H).

EXAMPLE 5

3-[2-((5-Methyl-2-phenyl-4-oxazolyl)methyl)benzofuran-5-yl-2-(propylthio)propanoic Acid To a solution of title product of Example 4 (3.8 g, 8.2 mmol) in methanol (100 ml) was added 1N sodium hydroxide (100 ml). The mixture was heated to reflux for 2 hours, cooled, poured onto ice (300 ml) and acidified with 6N hydrochloric acid, then extracted with ethyl acetate (500 ml), during which some precipitated solid was collected. The aqueous phase was extracted again with ethyl acetate (200 ml), the combined extracts were washed with water (300 ml) and brine (300 ml), dried over sodium sulfate and concentrated, leaving a yellow-orange solid. The solids were combined and recrystallized from ethyl acetate (150 ml) to give the title compound as an off-white solid (2.5 g, mp 169°-170° C.).

The following compounds were prepared by the same route from the corresponding ethyl esters:

3-[2-((5-Methyl-2-phenyl-4-oxazolyl)methyl)benzofuran-5-yl]-2-propanoic acid (mp 153°-154° C.)

2-Ethylthio-3-[2-((5-methyl-2-phenyl-4-oxazolyl)methyl)benzofuran-5-yl]propanoic acid (mp 144°-145° C.)

3-[2-((5-Methyl-2-phenyl-4-oxazolyl)methyl)benzofuran-5-yl]-2-(phenylthio)propanoic acid (mp 160°-16-1° C.)

3-[2-((5-Methyl-2-phenyl-4-oxazolyl)methyl)benzofuran-5-yl]-2-(octylthio)propanoic acid (mp 94°-96° C.)

EXAMPLE 6

3-[2-(5-Methyl-2-phenyl-4-oxazolyl)methylbenzofuran-5-yl]-2-(methylthio)propanoic Acid 5-Amino-2-[(5-methyl-2-phenyl-4-oxazolyl)methyl]-benzofuran was converted into the title compound according to the procedure of Example 2. Mp 178°-179° C.

3-[2-[5-Methyl-2-(3-methylphenyl)-4-oxazolyl]methyl]benzofuran-5-yl]-2-(methylthio)propanoic acid was prepared by the same procedure using the corresponding starting material. Mp 125°-127° C.

EXAMPLE 7

Ethyl 2-Acetylthio-3-[2-((5-methyl-2-phenyl-4-oxazolyl)methyl)benzofuran-5-yl]propanoate was prepared from ethyl alpha-bromo-2-(5-methyl-2-phenyl-4-oxazolyl)methyl-5-benzofuranpropanoic acid according to the procedure of Example 3 and obtained as an oil.

$^1$H NMR (CDCl$_3$, 300 MHz) delta 1.10 (t, J=7Hz, 3H), 2.29 (s, 3H), 2.34 (s, 3H), 3.04 (dd, J=7Hz, 14Hz, 1H), 3.25 (dd, J=8Hz, 14Hz, 1H), 3.99 (s, 2H), 4.07 (q, J=7Hz, 2H), 4.38 (dd, J=7Hz, 8Hz, 1H), 6.40 (s, 1H), 7.03 (dd, J=2Hz, 8Hz, 1H), 7.28 (s, 1H), 7.36-7.42 (m, 3H), 7.94-7.98 (m, 2H).

Ethyl 2-((Acetylthio)-3-[2-[(5-methyl-2-(3-methylphenyl)-4-oxazolyl)methyl]benzofuran-5-yl]propanoate was prepared according to the same procedure and obtained as an oil. $^1$H. NMR (CDCl$_3$, 300 MHz) delta 1.10 (t, J=7Hz, 3H), 2.30 (s. 3H), 2.35 (s, 3H), 2.40 (s, 3H), 3.05 (dd, J=7Hz, 14Hz, 1H), 3.27 (dd, J=8Hz, 14Hz, 1H), 4.00 (s, 2H), 4.07 (q, J=7Hz, 2H), 4.39 (dd, J=7Hz, 8Hz, 1H), 6.40 (s, 1H), 7.04 (dd, J=2Hz, 8Hz, 1H), 7.18 (d, J=8Hz, 1H), 7.26-7.30 (m, 3H), 7.75 (d, J=8Hz, 1H), 7.81 (s, 1H).

EXAMPLE 8

Ethyl 3-[2-((5-Methyl-2-phenyl-4-oxazolyl)methyl)benzofuran-5-yl]-2-(propylsulfinyl)propanoate To a solution of title product of Example 4 (0.39 g, 0.85 mmol) in tetrahydrofuran (75 ml) was added at 0° C., 80% m-chloroperoxybenzoic acid (0.18 g, 0.85 mmol). After 10 minutes, ethyl vinyl ether (0.5 ml) was added and the solution was diluted with ethyl acetate, washed with water (3×) and brine, dried over magnesium sulfate and concentrated. Flash-chromatography (hexanes/ethyl acetate, 2:1) gave the expected product as an oil (0.35 g).

$^1$H NMR (CDCl$_3$, 300 MHz) delta 1.05 (t, J=7Hz, 3/2H), 1.09 (t, J=7Hz, 3/2H), 1.12 (t, J=7Hz, 3/2H), 1.19 (t, J=7.1Hz, 3/2H), 1.73-1.94 (m, 2H), 2.34 (s, 3H), 2.56-2.88 (m, 2H), 3.27-3.46 (m, 2H), 3.71-3.78 (m, 1H), 4.01 (s, 2H), 4.05-4.26 (m, 2H), 6.41 (d, J=0.7Hz, 1/2H), 6.42 (d, J=1.0Hz, 1/2H), 7.04 (dd, J=1.7Hz, 6.9Hz, 1/2H), 7.07 {dd, J=1.8Hz, 6.7Hz, 1/2H), 7.30-7.33 (m, 2H), 7.36-7.43 (m, 3H), 7.92-8.03 (m, 2H).

EXAMPLE 9

3-[2-((5-Methyl-2-phenyl-4-oxazolyl)methyl)benzofuran-5-yl]-2-(methylsulfonyl)propionic acid To a solution of title product of Example 5 (0.30 g, 0.74 mmol) in tetrahydrofuran (75 ml) was added 80% m-chloroperoxybenzoic acid (0.16 g, 0.74 mmol) at 0° C. After 10 minutes, ethyl vinyl ether (0.5 ml) was added, the solution was diluted with ethyl acetate, washed with water (3×) and brine, dried over magnesium sulfate and concentrated. The product was isolated by flash-chromatography (hexane/ethyl acetate, 1:1) as a yellow solid (0.11 g, mp 220°-203° C.).

EXAMPLE 10

3-[2-((5-Methyl-2-phenyl-4-oxazolyl)methyl)benzofuran-5-yl]-2-(propylsulfinyl)propanoic Acid A solution of the title product of Example 8 (0.20 g, 0.42 mmol) in methanol (5 ml) and 1N sodium hydroxide (5 ml) was stirred at room temperature for 48 hours. It was then poured into water, acidified with concentrated hydrochloric acid and extracted with ethyl acetate (3×). The combined extracts were washed with water and brine, dried over sodium sulfate and concentrated to an oil. The product was purified by flash-chromatography (ethyl acetate/hexane, 10:1) and obtained as an oily solid (43 mg).

$^1$H NMR (CDCl$_3$, 300 MHz, 62° C.) delta 0.88 (t, J=7Hz, 3/2H), 0.97 (t, J=7Hz, 3/2H), 1.60 (m, 1H), 1.75 (m, 1H), 2.34 (s, 3/2H), 2.36 (s, 3/2H), 2.55-2.70 (m, 1H), 2.80 (m, 1/2H), 2.91 (m, ½H), 3.05 (m, 1/2H), 3.35 (m, 1H), 3.42-3.51 (m, 1.5H), 3.97 (s, 2/2H), 3.99 (s, 2/2H), 6.34 (s, 1/2H), 6.38 (s, 1/2H), 7.06 (d, J=7Hz, 1H), 7.20-7.27 (m, 1H), 7.31-7.37 (m, 4H), 7.92-7.95 (m, 2H).

EXAMPLE 11

3-[2-((5-Methyl-2-phenyl-4-oxazolyl)methyl)benzofuran-5-yl)-2-(methylthio)-N-(phenylsulfonyl)propanamide A mixture of the title product of Example 6 (0.15 g, 0.37 mmol) and thionyl chloride (0.10 ml, 1.4 mmol) was heated on a steam bath for 20 minutes. The mixture was cooled, diluted with benzene and concentrated. A mixture of benzenesulfonamide (0.12 g, 0.74 mmol) and 60% sodium hydride (32 mg, 0.81 mmol) in tetrahydrofuran (5 ml) was heated at reflux for 30 minutes, cooled to 0° C. and treated with a solution of this acid chloride in tetrahydrofuran (5 ml). The mixture was heated for 3 hours at reflux and overnight at room temperature. It was then diluted with ethyl acetate, washed with 1N hydrochloric acid, water (2×) and brine, dried over magnesium sulfate and concentrated. The product was purified by flash-chromatography (3% methanol in dichloromethane) and obtained as an oil.

$^1$H NMR (CDCl$_3$, 300 MHz) delta 1.90 (s, 3H), 2.36 (s, 3H), 2.92 (dd, J=8Hz, 14Hz, 1H), 3.14 (dd, J=8Hz, 14Hz, 1H), 3.38 (t, J=8Hz, 1H), 3.99 (s, 3H), 6.33 (s, 1H), 6.80 (dd, J=2Hz, 8Hz, 1H), 7.09 (d, J=2Hz, 1H), 7.17 (dd, J=2Hz, 8Hz, 1H), 7.38-7.60 (m, 6H), 7.94-7.98 (m, 4H), 9.00 (br s, 1H).

By the same method the following compounds were prepared: 3-[2-([5-Methyl-2-phenyl-4-oxazolyl)methyl)-benzofuran-5-yl]-2-(methylthio)-N-(phenylcarbonyl)-propanamide (mp 62° C.).

3-[2-((5-Methyl-2-phenyl-4-oxazolyl)methyl)benzofuran-5-yl]-2-(methylthio)-N-(4-chlorophenylsulfonyl)-propanamide (mp 94°-95° C.).

3-[2-((5-Methyl-2-phenyl-4-oxazolyl)methyl)benzofuran-5-yl]-2-(methylthio)-N-(4-fluorophenylsulfonyl)-propanamide (mp 60°-62° C.).

3-[2-(5-Methyl-2-phenyl-4-oxazolyl)methyl)benzofuran-5-yl]-2-(methylthio)-N-(methanesulfonyl)propana-mide (mp 63°-64° C.)

3-[2-((5-Methyl-2-phenyl-4-oxazolyl)methyl)benzofuran-5-yl]-2-(methylthio)-N-[(E)-2-phenylethenylsulfonyl]propanamide (oil).

$^1$H NMR (CDCl$_3$, 300 MHz) delta 2.05 (s, 3H), 2.34 (s, 3H), 3.02 (dd, J=8Hz, 14Hz, 1H), 3.25 (dd, J=8Hz, 14Hz, 1H), 3.48 (t, J=8Hz, 1H), 3.98 (s, 2H), 6.30 (s, 1H), 6.95 (d, J=14Hz, 1H), 6.96 (dd, J=2Hz, 8Hz, 1H), 7.22 (d, J=2Hz, 1H), 7.35-7.48 (m, 9H), 7.69 (d, J=14Hz, 1H), 7.95-8.0 (m, 2H), 9.20 (br s, 1H).

3-[2-(5-Methyl-2-phenyl-4-oxazolyl)methyl)benzofuran-5-yl]-2-(methylthio)-N-(2-naphthylsulfonyl)-propanamide (mp 163°-166° C.).

3-[2-((5-Methyl-2-phenyl-4-oxazolyl)methyl)benzofuran-5-yl]-2-(methylthio)-N-(N,N-diethylaminosulfonyl)propanamide (oil).

$^1$H NMR (CDCl$_3$, 300 MHz) delta 1.12 (t, J=7Hz, 6H), 2.08 (s, 3H), 2.36 (s, 3H), 2.96 (dd, J=8Hz, 14Hz, 1H), 3.30 (q, J=7Hz, 4H), 3.40 (t, J=8Hz, 1H), 4.00 (s, 2H), 6.41 (s, 1H), 7.01 (dd, J=2Hz, 8Hz, 1H), 7.26 (dd, J=2Hz, 1H), 7.30 (d, J=8Hz, 1H), 7.38-7.42 (m, 3H), 7.92-7.96 (m, 2H), 8.72 (s, 1H).

EXAMPLE 12

Optical Resolution of 3-[2-((5-methyl-2-phenyl-4-oxazolyl)methyl)benzofuran-5-yl]-2-(propylthio)propanoic Acid To a slurry of title product of Example 5 (1.6 g, 3.8 mmol) in benzene (35 ml) was added oxalyl chloride (1.8 ml, 21 mmol). Gas was evolved and the slurry turned into a clear yellow solution within 10 minutes. After two hours the solvent was removed, the residue was dissolved in dioxane (25 ml) and added dropwise to a solution of (S)-(+)-2-phenylglycinol (0.52 g, 3.8 mmol) and triethylamine (0.53 ml) in dioxane (10 ml). After 2 hours, the solvent was removed, water was added to the residue and the mixture was acidified with 6N hydrochloric acid. The solid was collected, dried and recrystallized from ethyl acetate/hexanes then from ethyl acetate to give the less polar isomer (on silica thin-layer chromatography, hexane/ethyl acetate, 1:2) as a pale yellow solid (0.41 g). The combined mother liquors were concentrated and the products separated by flash-chromatography (hexane/ethyl acetate, 1:1). More of the less polar isomer was thus obtained (0.14 g) as well as the more polar isomer (0.39 g).

The less polar amide (0.54 g, 0.97 mmol) and p-toluenesulfonic acid (2.8 g, 15 mmol) were placed in water (20 ml) and isopropanol (20 ml) and heated to reflux for three days. The solution was cooled, diluted with water (75 ml) and extracted with ethyl acetate (2×75 ml). The combined extracts were washed with water (2×75 ml) and brine (75 ml), dried over sodium sulfate and concentrated. The product was purified by flash chromatography (hexanes/ethyl acetate/acetic acid, 16:4:1), then recrystallized from ethyl acetate (15 ml)/hexane (5 ml). The mother liquor was concentrated to give a white solid (83 mg, [alpha]$_D$= +8.8°, c=1.08, CDCl$_3$). This material was subsequently found to be greater than 95% optically pure by conversion back to the amide under neutral conditions (EEDQ) and its NMR spectrum was identical to the one of the racemic material.

In the same manner the more polar amide (0.39 g, 0.71 mmol) was converted into the levorotatory acid (81 mg, [alpha]$_D$= −9.4°, c=1.06, CDCl$_3$).

EXAMPLE 13

2-Methoxy-3-[4-[2-(5-methyl-2-phenyl-4-oxazolyl)ethoxy]phenyl]propanoic Acid

A.

4-[2-(5-Methyl-2-phenyl-4-oxazolyl)ethoxy]benzeneacetaldehyde

To a slurry of methoxymethyltriphenylphosphonium chloride (11 g, 32 mmol) in tetrahydrofuran (120 ml), cooled to 0° C., was added dropwise a 2.5M solution of n-butyllithium in hexanes (9.8 ml, 25 mmol). The red solution was stirred at 0° C. for 30 minutes then a solution of 4-[2-(5-methyl-2-phenyl-4-oxazolyl)ethoxy]benzaldehyde (Takeda U.S. Pat. No. 4,725,610) (5.0 g, 16 mmol) in tetrahydrofuran (70 ml) was added dropwise. The mixture was allowed to warm to room temperature and stirred overnight. It was then diluted with water and extracted with ethyl acetate (3×). The combined extracts were washed with water (2×) and brine, dried over sodium sulfate and concentrated. The product, a mixture of E and Z 4-[2-[4-(2-methoxyethenyl)phenoxy]ethyl]-5-methyl-2-phenyloxazole, was isolated by flash-chromatography (hexanes/ethyl acetate, 2:1) as a yellow solid (2.6 g).

This solid (2.0 g, 6.0 mmol) was dissolved in tetrahydrofuran (100 ml) and 35% perchloric acid (10 ml) was added. The solution was heated to reflux for 1 hour then stirred overnight at room temperature, then diluted with water and extracted with ethyl acetate (2×). The combined extracts were washed with water and brine, dried over sodium sulfate and concentrated. The residue was purified by flash-chromatography (hexane/ethyl acetate, 4:1) and a yellow solid (0.51 g) was obtained.

B. Ethyl alpha-hydroxy-4-[2-(5-methyl-2-phenyl-4-oxazolyl)ethoxy]benzenepropanoate To a solution of 4-[2-(5-methyl-2-phenyl-4-oxazolyl)ethoxy]benzeneacetaldehyde (0.51 g, 1.6 mmol) and trimethylsylyl cyanide (0.21 ml, 1.6 mmol) in deuterochloroform (1 ml) was added zinc iodide (1 crystal). The solution was stirred overnight at room temperature, then concentrated to yield the product, 4-[2-(5-methyl-2-phenyl-4-oxazolyl)ethoxy]-alpha(trimethylsilyloxy)benzenepropanenitrile as an oil.

This oil was dissolved in hydrogen chloride (50 ml), the solution was cooled to 0° C., saturated with hydrogen chloride, and stirred overnight at room temperature, then saturated with hydrogen chloride again and stirred another 24 hours at room temperature. The mixture was poured into water, ethyl acetate was added, then 1N sodium hydroxide so as to get the product in solution. The organic layer was separated, washed with water and brine, dried over sodium sulfate and concentrated to a brown oil which was purified by flash-chromatography (hexanes/ethyl acetate, 3:2). The pure product was obtained as an oil (0.19 g).

C.

2-Methoxy-4-3-[2-(5-methyl-2-phenyl-4-oxazolyl)ethoxy)phenylpropanoic acid

A 60% sodium hydride dispersion (40 mg) was washed with hexane and suspended in tetrahydrofuran (10 ml). A solution of ethyl alpha-hydroxy-4-[2-(5-methyl-2-phenyl-4-oxazolyl)ethoxy]benzenepropanoate (0.19 g, 0.48 mmol) in tetrahydrofuran (2 ml) was added and after 10 minutes methyl iodide (0.3 ml, 4.8 mmol) was added. The mixture was stirred at room temperature overnight, then diluted with water, acidified with 2N hydrochloric acid and extracted with ethyl acetate (2×). The combined extracts were washed with water and brine, dried over sodium sulfate and concentrated. The product was purified by flash-chromatography (hexanes/ethyl acetate/acetic acid, 10:10:1) and obtained as a yellow sticky solid.

$^1$H NMR (CDCl$_3$, 300 MHz) delta 2.36 (s, 3H), 2.96 (m, 3H), 3.05 (dd, J=6Hz, 14Hz, 1H), 3.37 (s, 3H), 3.93 (dd, J=6Hz, 9Hz, 1H), 4.17 (t, J=9Hz, 2H), 6.79 (d, J=8Hz, 1H), 7.10 (d, J=8Hz, 1H), 7.36–7.40 (m, 3H), 7.92 –7.96 (m, 2H).

EXAMPLE 14

2-Methoxy-3[2-((5-methyl-2-phenyl-4-oxazolyl)methyl)benzofuran-5-yl]propanoic Acid A. 4-Benzoylamino-1-hexyn-5-one Acetic anhydride (150 ml) was added to a solution of 2-benzoylamino-4-pentynoic acid (J. Org. Chem. 1983, 48, 3318) (73 g, 0.34 mol) in pyridine (200 ml) and the solution was heated to 90° C. for 1 hour, then allowed to cool to 60° C. and water (150 ml) was added. The mixture was heated to 85°–90° C. for 20 minutes, then cooled, diluted with water (300 ml) and extracted with chloroform (2×400 ml). The combined extracts were washed with water, 1N hydrochloric acid (3×500 ml), sodium bicarbonate and brine, and dried over magnesium sulfate. The chloroform solution was decolorized with charcoal, filtered and concentrated. The residue was recrystallized from butyl chloride to yield a tan solid (51 g, mp 101°–103° C.).

B. 5-Methyl-2-phenyl-4-(2-propynyl)oxazole

A solution of 4-benzoylamino-1-hexyn-5-one (30 g, 0.14 mol) in trifluoroacetic anhydride (100 ml) and trifluoroacetic acid (200 ml) was heated to 35°–40° C. for 6 hours. The solution was concentrated and the residue taken up in ethyl acetate (400 ml). To this solution was added saturated sodium bicarbonate solution 400 ml)

followed by solid sodium bicarbonate until the water layer became neutral. The layers were separated, the organic layer was washed with brine, dried over magnesium sulfate and concentrated to give a brown oil (28 g) which was used as such.

C.
2-(5-Methyl-2-phenyl-4-oxazolyl)methyl-5-benzofurancarboxaldehyde

To a slurry of cuprous oxide (12 g, 84 mmol) in pyridine (150 ml) were added a solution of 5-methyl-2-phenyl-4-(2-propynyl)oxazole in pyridine (150 ml) followed by a solution of 4-hydroxy-3-iodobenzaldehyde (35 g, 0.14 mol) in pyridine (100 ml). Bis(triphenylphosphine)palladium (II) chloride (0.50 g, 0.7 mmol) was then added as a solid and the mixture was heated to reflux overnight. The mixture was cooled and concentrated. The residue was taken up in ethyl acetate (250 ml+3×50 ml). The ethyl acetate solution was concentrated and the residue was extracted with hot cyclohexane. The hot solution was filtered and cooled and the solid was collected (29 g).

D.
5-(2-Methoxyethenyl)-2-[(5-methyl-2-phenyl-4-oxazolyl)methyl]benzofuran

To a slurry of methoxymethylphosphonium chloride (34 g, 0.10 mol) and diisopropylamine (9.9 ml, 75 mmol) in tetrahydrofuran (500 ml) was added a 2.5M n-butyllithium solution in hexanes (30 ml, 75 mmol), at −10° C. After 1 hour at 10° C. a solution of 2-(5-methyl-2-phenyl-4-oxazolyl)methyl-5-benzofurancarboxaldehyde (16 g, 50 mmol) in tetrahydrofuran (200 ml) was added. The mixture was allowed to warm to room temperature over 2 hours, then poured into water (600 ml) and extracted with ether (3×). The combined extracts were washed with brine, dried over magnesium sulfate and concentrated. The product was isolated by flash-chromatography (hexanes/ethyl acetate, 4:1) as a solid (14 g).

E.
5-(2,2-Dimethoxyethyl)-2-[(5-methyl-2-phenyl-4-oxazolyl)methyl]benzofuran A solution of 5-(2-methoxyethenyl)-2-(5-methyl-2-phenyl-4-oxazolyl)methylbenzofuran (0.69 g, 2.0 mmol) and p-toluenesulfonic acid monohydrate (40 mg, 0.21 mmol) in methanol (30 ml) was heated to reflux overnight. The solvent was removed, the residue was taken up in ethyl acetate, the solution was washed with 5% sodium bicarbonate and brine, dried over magnesium sulfate and concentrated to an oil which slowly solidified on standing (0.75 g).

F.
2-Methoxy-3-[2-((5-methyl-2-phenyl-4-oxazolyl)methyl)benzofuran-5-yl]propanenitrile To a solution of 5-(2,2-dimethoxyethyl)-2-[(5-methyl-2-phenyl-4-oxazolyl)methyl]benzofuran (0.75 g, 2.0 mmol) in dichloromethane (15 ml) were added trimethylsilyl cyanide (0.80 ml, 6.0 mmol) and boron trifluoride etherate (50 μl, 0.5 mmol). After 1 hour the solution was diluted with dichloromethane, washed with 5% sodium bicarbonate, water and brine, dried over magnesium sulfate and concentrated. The product was purified by flash-chromatography (hexanes/ethyl acetate, 2:1) and isolated as a solid (0.64 g, mp 107°-109° C.).

G.
2-Methoxy-3-[2-((5-methyl-2-phenyl-4-oxazolyl)methyl)benzofuran-5-yl]propanoic acid A mixture of 2-methoxy-3-[2-((5-methyl-2-phenyl-4-oxazolyl)methyl)benzofuran-5-yl]propanenitrile (0.64 g, 1.7 mmol), ethanol (30 ml) and 6N sodium hydroxide (10 ml) was heated to reflux for 3 hours. Water (30 ml) was added and the solution was acidified with concentrated hydrochloric acid (6 ml), then extracted with ethyl acetate (2×). The combined organic layers were washed with brine, dried over magnesium sulfate and concentrated. The product was recrystallized from ethyl acetate/hexanes and obtained as a white solid (0.47 g, mp 159°-160.5° C.).

Using the corresponding alcohols, the following compounds were prepared by the same procedure:

2-Ethoxy-3-[2-((5-methyl-2-phenyl-4-oxazolyl)methyl)benzofuran-5-yl]propanoic acid (mp 164°-165.5° C.)

3-[2-((5-Methyl-2-phenyl-4-oxazolyl)methyl)benzofuran-5-yl]-2-propoxypropanoic acid (mp 139.5°-140.5° C.)

3-[2-(5-Methyl-2-phenyl-4-oxazolyl)methyl)benzofuran-5-yl]-2-(2-propenyloxy)propanoic acid (mp 154°-155.5° C.)

3-[2-((5-Methyl-2-phenyl-4-oxazolyl)methyl)benzofuran-5-yl]-2-(phenylmethoxy)propanoic acid (mp 123°-126° C.)

2-(3-Hydroxypropoxy)-3-[2-((5-methyl-2-phenyl-4-oxazolyl)methyl)benzofuran-5-yl]propanoic acid (mp 125°-127° C.)

3-[2-(5-Methyl-2-phenyl-4-oxazolyl)methyl)benzofuran-5-yl]-2-(2-propynyloxy)propanoic acid (mp 148°-150° C.)

From (2H)-3,4-dihydro-2-[(4-(phenylmethoxy)phenyl)methyl]-6-benzopyrancarboxaldehyde (U.S. Pat. No. 4,798,835), sodium (2H)-3,4-dihydro-alpha-ethoxy-2-(4-phenylmethoxy)phenylmethyl-6-benzopyranpropanoate was prepared by the same sequence. Mp 61°-64° C.

EXAMPLE 15

2-Methoxy-3-[2-((5-methyl-2-phenyl-4-oxazolyl)methyl)benzofuran-5-yl]propanamide A solution of the Step F intermediate, Example 14 (0.24 g, 0.64 mmol) in ethanol (20 ml) was saturated with hydrogen chloride and stirred at room temperature for three days. The solvent was removed, water was added followed by saturated sodium bicarbonate to bring the pH to neutral. This mixture was extracted with ethyl acetate (2×), the combined extracts were washed with brine and dried over magnesium sulfate overnight. The product was isolated by flash-chromatography (hexanes/ethyl acetate, 1:1) as a white solid (58 mg, mp 164°-167° C.).

2-Ethoxy-3-[2-((5-methyl-2-phenyl-4-oxazolyl)methyl)benzofuran-5-yl]propanamide was obtained by the same method. Mp 165°-168° C.

EXAMPLE 16

(E) and (Z)-3-[2-((5-Methyl-2-phenyl-4-oxazolyl)methyl)benzofuran-5-yl]-2-methoxy-2-propenamide

A. (E) and (Z)-3-[2-((5-Methyl-2-phenyl-4-oxazolyl)methyl)benzofuran-5-yl]-2-methoxy-2-propenenitrile To a slurry of 60% sodium hydride (88 mg, 2.2 mmol) in dimethylformamide (15 ml) was added at 45° C. methoxyacetonitrile (0.21 g, 3.0 mmol). This solution was allowed to cool and after 30 minutes was slowly added to a warm (50° C) solution of 2-(5-methyl-2-phenyl-4-oxazolyl)methyl-5-benzofuran carboxaldehyde (Example 14) (0.63 g, 2.0 mmol) in dimethylformamide (10 ml). The mixture was heated to 75°-80° C. for 1 hour then cooled and poured into a water/ethyl acetate mixture. The layers were separated, the aqueous layer was extracted with ethyl acetate, the combined organic phases were washed with water (3×), dried over sulfate and concentrated. Flash-chromatography (hexanes-/ethyl acetate, 2.5:1) afforded the two geometrical isomers of the product, the less polar isomer (assigned as Z) as a solid (0.10 g), and the more polar isomer (E) as an oil (0.15 g).

B. (Z)-3-[2-(5-methyl-2-phenyl-4-oxazolyl)methyl-5-benzofuranyl]-2-methoxy-2-propenamide A solution of (Z)-3-[2-(5-methyl-2-phenyl-4-oxazolyl)methyl-5-benzofuranyl]-2-methoxy-2-propenenitrile (0.10 g, 0.27 mmol) in methanol (10 ml) and sodium hydroxide (2 ml) was heated to reflux for 3 hours then cooled, acidified with 6N hydrochloric acid and extracted with ethyl acetate. The combined extracts were washed with brine, dried over magnesium sulfate and concentrated. The product was purified by flash chromatography (ethyl acetate/methanol/acetic acid, 75:1:1) and obtained as a solid (31 mg, m.p. 166°-169° C.).

The (E) isomer was subjected to the same hydrolysis conditions, and the product isolated as a solid (26 mg, m.p. 160°-164° C.)

EXAMPLE 17

(E)-3-[2-(5-Methyl-2-phenyl-4-oxazolyl)methyl-5-benzofuranyl]-2-phenoxy-2-propenamide

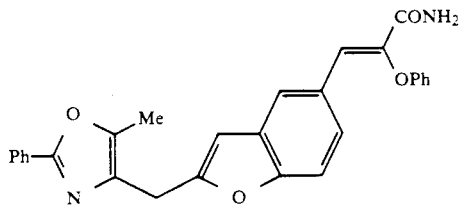

A. (E)-3-[2-(5-Methyl-2-phenyl-4-oxazolyl)methyl-5-benzofuranyl]-2-phenoxy-2-propenenitrile To a slurry of 60% sodium hydride (0.10 g, 2.5 mmol) in dimethylformamide (15 ml) was added at 60° C. phenoxyacetonitrile (0.21 g, 3.0 mmol). This solution was kept at 60° C. for 40 minutes, cooled to room temperature and was slowly added to a warm (80° C.) solution of 2-(5-methyl-2-phenyl-4-oxazolyl)methyl-5-benzofurancarboxaldehyde (0.40 g, 2.5 mmol) in dimethylformamide (20 ml). The mixture was heated to 75°-80° C. for 15 minutes, then cooled and poured into a solution of water (50 ml) and 1N HCl (2.5 ml). The mixture was extracted with ethyl acetate (2×). The combined organic phases were washed with water (3×) and brine, dried over magnesium sulfate and concentrated. Flash chromatography (hexanes/ethyl acetate/triethylamine, 50:50:1) afforded the product as an oil (0.19 g).

B. (E)-3-[2-(5-Methyl-2-phenyl-4-oxazolyl)methyl)-5-benzofuranyl]-2-phenoxy-2-propenamide A solution of (E)-3-[2-(5-methyl-2-phenyl-4-oxazolyl)methyl-5-benzofuranyl]-2-phenoxy-2-propenenitrile (0.19 g, 0.44 mmol) in ethanol (10 ml) and sodium hydroxide (2 ml) was heated to reflux for 24 hours, then cooled, poured into a mixture of water (50 ml) and ethyl acetate and acidified with 6N hydrochloric acid. The layers were separated, the aqueous layer was extracted with ethyl acetate and the combined organic phases were washed with brine, dried over magnesium sulfate and concentrated. The product was purified by flash chromatography (hexanes/ethyl acetate/acetic acid, 48:8:1) followed by recrystallization from ethyl acetate/hexanes (30 mg, m.p. 171°-172.5° C.).

EXAMPLE 18

Sodium 2-benzyloxy-3-[2-(4-benzyloxybenzyl)-3,4-dihydro-2H-benzofuran-6-yl]propanoate

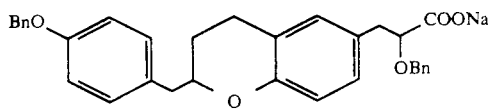

A. 2-(4-Benzyloxybenzyl)-3,4-dihydro-6-(2-methoxyethenyl)-2H-benzopyran

To a slurry of methoxymethylphosphonium chloride (12.5 g, 37 mmol) and diisopropylamine (9.9 ml, 27.5 mmol) in tetrahydrofuran (40 ml) was added a 2.5M n-butyllithium solution in hexanes (5.5 ml, 27.5 mmol) at −10° C. After 1 hour at −10° C. a slurry of 2-(4-benzyloxy)benzyl-3,4-dihydro-6-formyl-2H-benzopyran (U.S. Pat. No. 4,798,835) (4.9 g, 18 mmol) in tetrahydrofuran (100 ml) was added. The mixture was allowed to warm to room temperature over 2 hours, then was poured into water (200 ml) and extracted with ethyl acetate (3×). The combined extracts were washed with brine, dried over magnesium sulfate and concentrated. The product was isolated by flash chromatography (hexanes/ethyl acetate, 4:1) as an oil (2.1 g).

B. 2-(4-Benzyloxybenzyl)-6-[2,2-bis(benzyloxy)ethyl]-3,4-dihydro-2H-benzopyran A solution of 2-[(4-benzyloxy)benzyl]-3,4-dihydro-6-(2-methoxyethenyl)-2H-benzopyran (0.29 g, 0.75 mmol) and benzyl alcohol (1.0 ml. 9.7 mmol) containing Amberlyst 15 ® ion-exchange resin (100 mg) was heated to reflux overnight. The resin was filtered and washed with chloroform, the chloroform and the bulk of the benzyl alcohol were removed in vacuo and the residue was purified by flash chromatography (hexanes/ethyl acetate, 4:1) to give the pure product as an oil (0.40 g).

C. 2-Benzyloxy-3-[2-(4-benzyloxybenzyl)-3,4-dihydro-2H-benzopyran-6-yl]propanenitrile To a mixture of 2-[(4-benzyloxy)benzyl]-6-[2,2-bis(-benzyloxy)ethyl]-3,4-dihydro-2H-benzopyran (0.40 g, 0.70 mmol) and trimethylsilyl cyanide (2 ml) was added boron trifluoride etherate (2.0 6 ml, 0.2 mmol). After 1 hour the reaction was quenched with saturated sodium bicarbonate and the solution was extracted with ethyl acetate (2×). The combined extracts were washed with brine, dried over magnesium sulfate and concentrated. The product was purified by flash chromatography (hexanes/ethyl acetate, 2:1) and isolated as an oily solid (0.23 g).

D. Sodium 2-benzyloxy-3-[-2-(4-benzyloxybenzyl)-3,4-dihydro-2H-benzopyran-6-yl]propanoate A mixture of 2-benzyloxy-3-[2-(4-benzyloxybenzyl)-3,4-dihydro-2H-benzopyran-6-yl]propanenitrile (0.23 g, 0.47 mmol), ethanol (10 ml) and 6N sodium hydroxide (2 ml) was heated to reflux for 5 hours. Water (50 ml) was added and the solution was acidified with concentrated hydrochloric acid (2 ml), then extracted with ethyl acetate (2×). The combined organic layers were washed with brine, dried over magnesium sulfate and concentrated to an oil (0.19 g). The product was dissolved in methanol and treated with sodium methoxide (21 mg). The solvent was removed and the solid dried (7 mg, m.p. 165°–169° C.).

EXAMPLE 19
(S)-2-Ethoxy-3-{2-[5-methyl-2-phenyl-4-oxazolyl)methyl]benzofuran-5-yl}propanoic acid

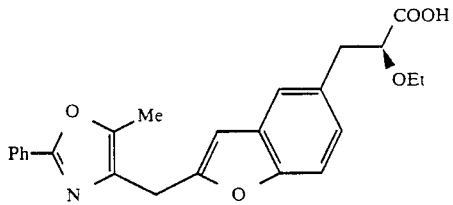

A. (S)-4-Benzyl-3-(ethoxyacetyl)oxazolidin-2-one

To a solution of (S)-4-benzyloxazolidin-2-one (4.4 g, 25 mmol) in dry tetrahydrofuran (20 ml), cooled to −78° C., was added n-butyllithium (2.5M solution in hexane, 10 ml, 25 mmol) dropwise. Another 20 ml of tetrahydrofuran was added to facilitate stirring. A solution of ethoxyacetyl chloride (3.0 g, 25 mmol) in tetrahydrofuran (5 ml) was added and the mixture was stirred at −78° C. for 30 minutes, then warmed to room temperature, poured into water and extracted with ethyl acetate (3×). The combined extracts were washed with water and brine, dried over sodium sulfate and concentrated to a yellow oil (4.3 g, [α]$_D$=56.7°).

B. 5-{(1R,2S)-1-hydroxy-2-ethoxy-3-[(S)-4-benzyl-2-oxo-3-oxazolidinyl]-3-oxopropyl}-2-[(5-methyl-2-phenyl-4-oxazolyl)methyl]benzofuran To a solution of (S)-4-benzyl-3-(ethoxyacetyl)oxazolidin-2-one (1.0 g, 3.8 mmol) in dichloromethane (10 ml), cooled to 0° C., was added freshly distilled dibutyl boron triflate (1.1 ml, 4.6 mmol) dropwise, followed by triethylamine (0.69 m), 4.9 mmol). After 5 minutes the solution was cooled to −78° C. and a precooled solution of 2-(5-methyl-2-phenyl-4-oxazolyl) methyl-5-benzofurancarboxaldehyde (1.33 g, 4.2 mmol) in dichloromethane (5 ml) was added. After 20 minutes the mixture was warmed to 0° C. and stirred at that temperature for 1 hour then quenched with a solution of pH 7 buffer (10 ml) in methanol (30 ml), followed by a solution of 30% hydrogen peroxide (10 ml) in methanol (30 ml), and stirred at 0° C. for 1 hour. The mixture was then diluted with water and extracted with ethyl acetate (3×). The combined extracts were washed with brine, dried over sodium sulfate and concentrated. The product was purified by flash chromatography (hexanes/ethyl acetate, 1:1) and obtained as a yellow solid (1.16 g, m.p. 66° C.).

C. 5-{(S)-2-Ethoxy-3-[(S)-4-benzyl-2-oxo-3-oxazolidinyl]-3-oxopropyl}-2-[(5-methyl-2-phenyl-4-oxazolyl)methyl]benzofuran To a solution of 5-{(1R,2S)-1-hydroxy-2-ethoxy-3-[(S)-4-benzyl-2-oxo-3-oxazolidinyl]-3-oxopropyl}-2-[(5-methyl-2-phenyl-4-oxazolyl)methyl]benzopyran (1.0 g, 1.72 mmol) in trifluoroacetic acid (20 ml) was added triethylsilane (3.0 ml, 19 mmol). The solution was stirred for 4 days at room temperature then diluted with ethyl acetate, washed with water and saturated sodium bicarbonate solution (3×), dried over sodium sulfate and concentrated. The product was isolated by flash chromatography (hexanes/ethyl acetate, 5:1) as a pale yellow solid (0.44 g).

D. (S)-2-Ethoxy-3-{2-[(5-methyl-2-phenyl-4-oxazolyl)methyl]benzofuran-5-yl}propanoic acid 5-((S)-2-Ethoxy-3[(S)-4-benzyl-2-oxo-3-oxazolidinyl]-3-oxopropyl}-2-[(5-methyl-2-phenyl-4-oxazolyl)methyl]benzofuran (0.15 g, 0.26 mmol) was dissolved in tetrahydrofuran (5 ml). The solution was cooled to 0° C. and 0.5N lithium hydroxide (1.1 ml, 0.52 mmol) was added. After 15 minutes the bulk of the ethanol was removed, the residue was acidified with 1N HCl, diluted with water and extracted with ethyl acetate (3×). The combined extracts were washed with brine, dried over sodium sulfate and concentrated. The product was purified by flash chromatography (hexanes/ethyl acetate/acetic acid, 10:10:1) then recrystallized from hexanes/ethyl acetate and obtained as a white solid (48 mg, m.p. 129° C., [α]$_D$=−12.5° (c 0.99, CDCl$_3$)):

Using the appropriate reagents, the following compounds were prepared by the same procedure.

(R)-2-Ethoxy-3-{2-[(5-methyl-2-phenyl-4-oxazolyl)methyl]benzofuran-5-yl}propanoic acid (m.p. 129° C., [α]$_D$=+9.3° (c 0.65, CDCl$_3$)).

(R)-3-(2-[(5-Methyl-2-phenyl-4-oxazolyl)methyl]benzofuran-5-yl}-2-phenoxypropanoic acid (m.p. 174°–175° C., [α]$_D$=−13.1° (c 0.50, CDCl$_3$)).

(S)-3-{2-[(5-Methyl-2-phenyl-4-oxazolyl)methyl]benzofuran-5-yl}-2-phenoxypropanoic acid (m.p. 165° C., [α]$_D$=+8.1° (c 0.07, CDCl$_3$)).

EXAMPLE 20

3-{[4-(4-Benzyloxyphenyl)ethoxy]phenyl}-2-methoxypropanoic acid

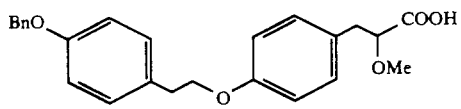

A. 1-Benzyloxy-4-(2-hydroxyethyl)benzene

To a solution of 4-hydroxyphenethyl alcohol (33 g, 0.24 mol) in dry dimethylformamide (200 ml), cooled to 0° C., was added potassium tert-butoxide (29 g, 0.26 mol) by portions. After 10 minutes, benzyl bromide (41 g, 0.28 mol) was added slowly. The reaction mixture was stirred for 15 minutes at 0° C., then for 3 hours at room temperature and was quenched with water (200 ml). The precipitate was collected, dried and recrystallized from isopropyl ether/hexanes (34 g).

B. 4-[(4-Benzyloxyphenyl)ethoxy]benzonitrile

To a suspension of sodium hydride (60%, 2.2 g, 55 mmol) in dry tetrahydrofuran (250 ml) was added a solution of 1-benzyloxy-4-(2-hydroxyethyl)benzene (11.4 g, 50 mmol) in tetrahydrofuran (50 ml). The reaction was heated to 40° C. for 1 hour. 4-Fluorobenzonitrile (6.7 g, 55 mmol) was added and the mixture was heated to reflux for 5 hours, cooled and neutralized with concentrated HCl. The precipitate was filtered, the filtrate was concentrated to dryness and the resulting solid was recrystallized from ethanol (12 g).

C. 4-[(4-Benzyloxyphenyl)ethoxy]benzaldehyde 4-(4-Benzyloxyphenyl)ethoxy]benzonitrile (4.9 g, 15 mmol) was dissolved in toluene (300 ml) and treated with a 1.5M toluene solution of diisobutylaluminum hydride (10 ml, 15 mmol). The reaction mixture was stirred overnight then quenched with a saturated sodium potassium tartrate solution (100 ml). The organic layer was washed with 5% sulfuric acid (50 ml), saturated sodium bicarbonate (100 ml) and brine, dried over magnesium sulfate and concentrated to dryness. The product was purified by flash chromatography (hexanes/ethyl acetate, 5:1) and obtained as an oil (4.0 g).

This aldehyde was converted into 2-methoxy-3-{[4-(4-benzyloxyphenyl)ethoxy]phenyl}propanoic acid (m.p. 65°–69° C.) by the sequence described in Example 18.

Using the appropriate reagents, the following compounds were prepared by the same procedure.

3-{[4-(4-Benzyloxyphenyl)ethoxy]phenyl}-2-ethoxypropanoic acid (m.p. 62°–63.5° C.).

3-{[4-(4-(3-Fluorobenzyloxy)phenyl)ethoxy]phenyl}-2-methoxypropanoic acid (m.p. 58°–62° C.).

2-Ethoxy-3-{[4-(4-(3-fluorobenzyloxy)phenyl)ethoxy]phenyl}propanoic acid (m.p. 54.5°–57.5° C.).

2-Benzyloxy-3-{[4-(4-benzyloxyphenyl)ethoxy]phenyl}propanoic acid (m.p. 85°–86° C.).

3-[3-(5-Ethyl-2-pyridyl)propoxy]phenyl-2-methoxypropanoic acid (m.p. 81°–82° C.).

2-Ethoxy-3-[3-(5-ethyl-2-pyridyl)propoxy]phenylpropanoic acid (m.p. 80°–81° C.).

3-[3-(5-Ethyl-2-pyridyl)propoxy]phenyl-2-propoxypropanoic acid (m.p. 89°–90° C.).

2-Ethoxy-3-(4-[3-(5-methyl-2-phenyl-4-oxazolyl)propanoyl]phenyl}propanoic acid (oil)

$^1$H NMR (250 MHz, CDCl$_3$) δ1,11 (t, J=6.9 Hz, 3H), 2.37 (s, 3H), 2.92 (t, J=7.1 Hz, 2H), 2.94–3.09 (m, 2H}, 3.13 (dd, J=13.9 Hz, 4.04 Hz, 1H), 3.35 (t, J=7.1 Hz, 3H), 3.60 (m, 1H), 3.61 (dd, J=9.1 Hz, 7.0 Hz, 1H), 7.32 (d, J=8.3 Hz, 2H), 7.36–7.44 (m, 3H), 7.89 (d, J=8.3 Hz, 2H), 7.94–7.98 (m, 2H), 8.95 (br s, 1H).

EXAMPLE 21

3-[2-(4-Benzyloxybenzyl)benzofuran-5-yl]-2-ethoxypropanoic acid

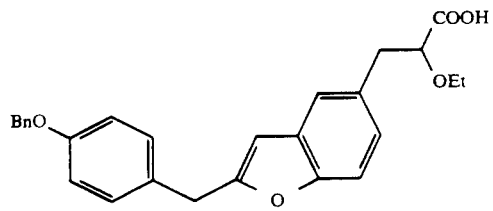

A. 5-Bromo-2-(4-benzyloxybenzoyl)benzofuran

5-Bromosalicylaldehyde (2.9 g, 14.5 mmol), cesium carbonate (2.5 g, 7.7 mmol) and acetonitrile (40 ml) were combined and heated to reflux for 30 minutes. The mixture was cooled to 0° C. and a solution of 4′-benzyloxy-2-bromoacetophenone (J. Het. Chem., 2, 310 (1965)) (4.7 g, 15 mmol) in acetonitrile (20 ml) was added. The cooling bath was removed, the mixture stirred at room temperature for 2.5 hours and the precipitate collected (4.5 g).

B. 5-Bromo-2-(4-benzyloxybenzyl)benzofuran

5-Bromo-2-(4-benzyloxybenzoyl)benzofuran (9.0 g, 22 mmol), sodium cyanoborohydride (10.4 g, 0.17 mol), zinc iodide (10.5 g, 0.35 mol) and 1,2-dichloroethane (350 ml) were combined and heated to reflux for 6 hours. The mixture was cooled, quenched with saturated ammonium chloride (500 ml), acidified with concentrated HCl and stirred for 30 minutes. The layers were separated, the aqueous layer was extracted with dichloromethane (400 ml) and the combined organic layers were washed with water and brine, dried over magnesium sulfate and concentrated, leaving a white solid (8.5 g).

C. 2-(4-Benzyloxybenzyl)-5-cyanobenzofuran

A mixture of 5-bromo-2-(4-benzyloxybenzyl)benzofuran (4.4 g, 11 mmol), copper cyanide (1.50 g, 17 mmol) and bis(triphenylphosphine) palladium (II) chloride (0.79 g, 1.1 mmol) in DMF (40 ml) was heated to reflux overnight. The mixture was cooled, ethyl acetate (200 ml) and concentrated ammonium hydroxide (100 ml) were added. The organic layer was washed with water (3×) and brine, dried over magnesium sulfate and concentrated. The product was purified by flash chromatography (hexanes/ethyl acetate, 5:1) and obtained as a solid (2.6 g, m.p. 131.5°–132.5° C.). This compound was transformed into the corresponding aldehyde as in Example 20 and into 3-[2-(4-benzyloxybenzyl)benzofuran-5-yl]-2-ethoxypropanoic acid (m.p. 91°–94° C.) by the sequence described in Example 18.

The following compounds were prepared by the same sequence from the appropriate starting materials and reagents.

3-[2-(4-Benzyloxybenzyl)benzofuran-5-yl]-2-methoxypropanoic acid (m.p. 98°–100° C.).

2-Benzyloxy-3-[2-(4-benzyloxybenzyl)benzofuran-5-yl]propanoic acid (m.p. 115°–116.5° C.).

EXAMPLE 22

(S)-3,4-Dihydro-2-ethoxy-{(R)-2-[4-(3-fluorobenzyloxy)benzyl]-2H-benzopyran-6-yl}propanoic acid

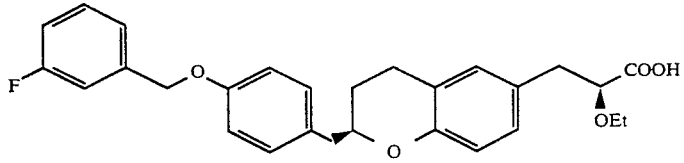

A.
(R)-(−)-3,4-Dihydro-2-(4-methoxybenzyl)-2H-benzopyran (R)-(−)-3,4-Dihydro-2-trifluoromethanesulfonyloxymethyl-2H-benzopyran (23.0 g, 78 mmol) and copper (I) bromide dimethyl sulfide complex (2.8 g, 13 mmol) were dissolved in tetrahydrofuran (400 ml) under a nitrogen atmosphere and cooled to −10° C., 4-Anisylmagnesium bromide (215 ml of a 1M solution in tetrahydrofuran, 0.215 mol) was added dropwise over 30 minutes, keeping the temperature below −5° C. The solution was stirred for 3 hours at 0° C. and then slowly poured into a mixture of water (800 ml) containing ammonium chloride (96 g, 1.8 mol) and methylene chloride (400 ml). The layers were separated and the aqueous portion was extracted with methylene chloride (400 ml). The combined organics were washed with 10% ammonium chloride (2×400 ml), water (250 ml), and brine (250 ml). The methylene chloride layer was dried (MgSC4), filtered and concentrated in vacuo. The residue was purified on silica gel using hexanes/methylene chloride (1:1) as eluent to afford 18.5 g (92% yield) of the title product as an oil. $[\alpha]_D$ −99.2° (c 1.7, MeOH); $^1$H NMR (300 MHz, CDCl$_3$) δ1.6–1.7 (m, 1H), 1.9–2.0 (m, 1H), 2.7–2.8 (m, 3H), 3.1 (dd, 1H), 3.8 (s, 3H), 4.1 (m, 1H), 6.8 (m, 3H), 7.0 (m, 2H), 7.2 (m, 2H).

B.
(R)-(−)-3,4-Dihydro-2-(4-hydroxybenzyl)-2H-benzopyran (R)-(−)-3,4-Dihydro-2-(4-methoxybenzyl)-2H-benzopyran (812 mg, 3.2 mmol), and lithium iodide (750 mg, 5.6 mmol) were dissolved in 2,4,6-collidine (2 ml) and heated to reflux for 24 hours. The reaction mixture was cooled, diluted with ethyl acetate (20 ml) and 10% HCl (20 ml), and stirred for 10 minutes. The layers were separated and the aqueous portion was extracted with ethyl acetate (50 ml). The combined organics were washed with water (20 ml), brine (20 ml), and were dried (MgSO$_4$). The solvent was removed in vacuo and the residue purified on silica gel using hexanes/ethyl acetate (3:1) as eluent to afford 730 mg of a colorless oil which crystallized upon standing, m.p. 60°–62° C.; $[\alpha]_D$ −110.2° (c 1.0, MeOH); $^1$H NMR (300 MHz, CDCl$_3$) δ1.7 (m, 1H), 2.0 (m, 1H), 2.7–2.8 (m, 3H), 3.1 (dd, 1H), 4.2 (m, 1H), 6.8 (m, 3H), 7.0–7.2 (m, 4H).

C.
(R)-(−)-2-(4-Acetoxybenzyl)-3,4-dihydro-2H-benzopyran (R)-(−)-3,4-Dihydro-2-(4-hydroxybenzyl)-2H-benzopyran (5.0 g, 20 mmol), 4-dimethylaminopyridine (240 mg, 2 mmol), triethylamine (2.6 g, 25 mmol) and acetic anhydride (2.9 g, 28 mmol) were dissolved in methylene chloride (75 ml) and stirred at room temperature for 2 hours under a nitrogen atmosphere. The solvent was removed in vacuo and the residue purified on silica gel using hexanes/ethyl acetate (3:1) as eluent to afford an oil which was crystallized from hexanes to yield 4.0 g of the title product, m.p. 64°–65° C.; $[\alpha]_D$ −98.9° (c 1.3, MeOH);
$^1$H NMR (300 MHz, CDCl$_3$) δ1.7 (m, 1H), 1.9 (m, 1H), 2.3 (s, 3H), 2.7 (m, 2H), 2.8 (dd, 1H), 3.1 (m, 1H), 4.2 (m, 1H), 6.8 (m, 2H), 7.0 (m, 3H), 7.2 (m, 2H).

D.
(R)-(−)-2-(4-Acetoxybenzyl)-3,4-dihydro-6-formyl-2H-benzopyran (R)-(−)-2-(4-Acetoxybenzyl)-3,4-dihydro-2H-benzopyran (16.6 g, 59 mmol), N-methylformanilide (23.9 g, 0.177 mol), and phosphorus oxychloride (18.0 g, 0.118 mol) were heated to 90° C. for 3 hours under a nitrogen atmosphere. The reaction mixture was cooled and poured into ice water (250 ml). The aqueous solution was extracted with ethyl acetate (2×500 ml) and the combined organics were washed with saturated NaHCO$_3$ (250 ml), water (250 ml), brine (250 ml), and dried (MgSC4). The solvent was removed in vacuo and the residue purified on silica gel using hexanes/ethyl acetate (3:1) as eluent to afford 15.7 g (86% yield) of the 6-formyl derivative,
$^1$H NMR (300 MHz CDCl$_3$) δ1.8 (m, 1H), 2.1 (m, 1H), 2.3 (s, 3H), 2.8 (m, 2H), 2.9 (m, 1H), 3.1 (m, 1H), 4.3 (m, 1H), 6.9 (d, 1H), 7.0 (d, 2H), 7.3 (d, 2H), 7.6 (m, 2H), 9.8 (s, 1H).

E.
(R)-(−)-3,4-Dihydro-6-formyl-2-(4-hydroxybenzyl)-2H-benzopyran (R)-(−)-2-(4-Acetoxybenzyl)-3,4-dihydro-6-formyl-2H-benzopyran (15.7 g, 51 mmol) was dissolved in a mixture of methanol (200 ml), tetrahydrofuran (200 ml) and 2M NaOH (200 ml) and stirred at room temperature for 2 hours. The reaction mixture was concentrated in vacuo, diluted with water (100 ml) and acidified with 10% HCl (250 ml). The aqueous solution was extracted with ethyl acetate (2×500 ml) and the combined organics were washed with water (250 ml), brine (250 ml), and dried (MgSO$_4$). The solvent was removed in vacuo and the residue was crystallized from hexanes/ethyl acetate (3:1) to afford 10.1 g of the title compound, m.p. 134°–135° C.; $[\alpha]_D$ −155.2° (c 1.0, MeOH);
$^1$NMR (300 MHz CDCl$_3$) δ1.6 (m, 1H), 1.9 (m, 1H), 2.8 (m, 3H), 3.0 (dd, 1H), 4.2 (m, 1H), 5.1 (br s, 1H, OH), 6.7 (d, 2H), 6.8 (d, 1H), 7.0 (d, 2H), 7.5 (m, 2H), 9.7 (s, 1H).

F.
(R)-2-[4-(3-Fluorobenzyloxy)benzyl]-3,4-dihydro-6-formyl-2H-benzopyran

To a solution of (R)-3,4-dihydro-6-formyl-2-(4-hydroxybenzyl)-2H-benzopyran (1.8 g, 6.7 mmol) in DMF (10 ml) at 0° C. was added potassium tertbutoxide (0.83 g, 7.4 mmol). After 30 minutes m-fluorobenzyl bromide (0.91 ml, 7.4 mmol) was added and the resulting slurry was warmed to room temperature and stirred for 2 hours. Water was added and the precipitate was collected, washed with water and air dried (2.5 g).

G. (R)-6-{(1R, 2S)-1-Hydroxy-2-ethoxy-3-[(S)-4-benzyl-2-oxo-3-oxazolidinyl]-3-oxopropyl}-2-[4-(3-fluorobenzyloxy)benzyl]-2H-benzopyran Trifluoromethanesulfonic acid (0.64 ml, 7.2 mmol) was added to a 1M solution of triethylborane in toluene (7.2 ml, 7.2 mmol) and the mixture was heated to 40° C. for 1 hour then cooled to 0° C. A solution of (S)-4-benzyl-3-(ethoxyacetyl) oxazolidin-2-one (Example 19) (0.64 g, 3.6 mmol) in dichloromethane (5 ml) was added, followed by diisopropylethylamine (1.33 ml, 7.6 mmol). After 30 minutes the solution was cooled to −78° C. and a solution of (R)-2-[4-(3-fluorobenzyloxy)benzyl]-3,4-dihydro-6-formyl-2H-benzopyran (1.0 g, 3.6 mmol) in dichloromethane (15 ml) was added. The mixture was stirred at −78° C. for 2 hours then 30 minutes at 0° C. and quenched with pH 7 buffer (5 ml). The mixture was diluted with ether, the organic layer was washed with water and brine, dried over magnesium sulfate and concentrated. The product was isolated by flash chromatography (hexanes/ethyl acetate, 3:2) as an oil (85 mg).

H.
(R)-6-{(S)-2-Ethoxy-3-[(S)-4-benzyl-2-oxo-3-oxazolidinyl]-3-oxopropyl}-2-[4-(3-fluorobenzyloxy)benzyl]-2H benzopyran (R)-6-{(1R, 2S)-1-Hydroxy-2-ethoxy-3-[(S)-4-benzyl-2-oxo-3-oxazolidinyl]-3-oxopropyl}-2-[4-(3-fluorobenzyloxy)benzyl]-2H-benzopyran (80 mg, 0.13 mmol) was dissolved in trifluoroacetic acid (2 ml) and triethylsilane (0.20 ml) was added. After 30 minutes the solution was diluted with ether, washed with water (2×) and saturated sodium bicarbonate (2×), dried over magnesium sulfate and concentrated. The product was purified by flash chromatography (hexanes/ethyl acetate, 2:1) and obtained as an oil (39 mg).

I.
(S)-2-Ethoxy-3-{(2R)-2-[4-(3-fluorobenzyloxy)benzyl]-3,4-dihydro-2H-benzopyran-6-yl}propanoic acid (R)-6-{(S) 2-Ethoxy-3-[(S)-4-benzyl-2-oxo-3-oxazolidinyl]-3-oxopropyl}-2-[4-(3-fluorobenzyloxy)benzyl]-2H-benzopyran (39 mg, 63 mmol) was dissolved in tetrahydrofuran (1.5 ml) at 0° C. and treated with 0.5N lithium hydroxide (1 ml). The reaction mixture was warmed to room temperature and stirred for 1 hour, then acidified with 1N hydrochloric acid and extracted with ethyl acetate (3×). The combined extracts were washed with water and brine, dried over magnesium sulfate and concentrated. The product was purified by flash chromatography (hexanes/ethyl acetate/acetic acid, 15:5:1) and isolated as an oil (30 mg).

$^1$H NMR (300 MHz, CDCl$_3$) δ1.16 (t, J=6.9 Hz, 3H), 1.67 (m, 1H), 1.93 (m, 1H), 2.68–2.72 (m, 2H), 2.79 (dd, J=13.8 Hz, 6.9 Hz, 1H), 2.88 (dd, J=14.4 Hz, 7.7 Hz, 1H), 3.00 (dd, J=12.2 Hz, 4.3 Hz, 1H), 3.05 (dd, J=13.4 HZ, 7.6 Hz, 1H), 3.43 (m, 1H), 3.58 (m, 1H), 4.01 (dd, J=7.5 Hz, 4.2 Hz, 1H), 4.12 (m, 1H), 5.03 (s, 2H), 6.71 (d, J=8.2 Hz, 1H), 6.88–7.02 (m, 3H), 6.89 (d, J=8.5 Hz, 2H), 7.12–7.18 (m, 2H), 7.17 (d, J=8.6 Hz, 2H), 7.32 (m, 1H).

The following compounds were prepared from the corresponding aldehydes (Example 20) by the same sequence.

(S) Sodium 2-ethoxy-3-{[4-(4-(3-fluorobenzyloxy)phenyl)ethoxy]phenyl}propanoate (m.p. 195°-200° C.).

(R) Sodium 2-ethoxy-3-{[4-(4-(3-fluorobenzyloxy)phenyl)ethoxy]phenyl}propanoate (m.p. 200°-205° C.).

EXAMPLE 23

Sodium 3,4-dihydro-2-ethoxy-3-[(R)-2-(4-benzyloxybenzyl)-2H-benzopyran-6-yl]propanoate

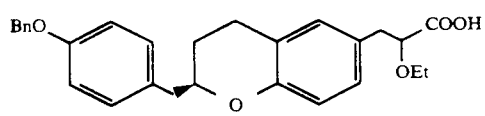

(R)-(−)-3,4-Dihydro-6-formyl-2-(4-hydroxybenzyl)-2H-benzopyran (Example 22) was transformed into the title compound by a sequence analogous to the one described in Example 18, m.p. 160°-170° C. (dec.).

Using the corresponding reagent, 3,4-dihydro-2-ethoxy-3-{(R)-2-[4-(5-ethyl-2-pyridyl)methoxy]-2H-benzopyran-6-yl}propanoate was prepared by the same method, m.p. 108°-109° C.

EXAMPLE 24

Sodium 3,4-dihydro-2-ethoxy-3-[(R)-2-benzyl-2H-benzopyran-6-yl-propanoate

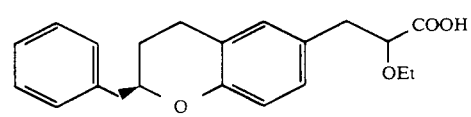

(R)-(−)-3,4-Dihydro-6-formyl-2-benzyl-2H-benzopyran was prepared from (R)-(−)-3,4-dihydro-2-trifluoromethanesulfonyloxymethyl-2H-benzopyran and phenylmagnesium bromide as described in Example 22 and converted to the title compound as in Example 18 (foam).

$^1$NMR (300 MHz, CDCl$_3$) δ1.2 (t, 3H), 1.7 (m, 1H), 2.0 (m, 1H), 2.8–3.1 (m, 6H), 3.4 (m, 1H), 3.6 (m, 1H), 4.0 (dd, 1H), 4.1 (m, 1H), 6.7 (d, 2H), 6.9 (s, 1H), 6.95 (dd, 1H), 7.2 (m, 5H).

EXAMPLE 25

2-Phenoxy-3-[4-(2-phenyl)ethoxyphenyl]propanoic acid

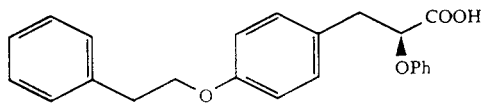

A.
(S)-4-Benzyl-3-[(1S),(2R)-2-(4-benzyloxyphenyl)-2-hydroxy-1-phenoxyethyl]-2-oxazolidinone Trifluoromethanesulfonic acid (5.0 ml, 56 mmol) was added to a solution of triethylborane in hexanes (56 ml of a 1M solution, 56 mmol). After the bubbling stopped, the solution was heated to 40° C. for 1 hour then cooled to 0° C., a solution of (S)-4-benzyl-3-(phenoxyacetyl)oxazolidin-2-one (prepared as in Example 19) (5.0 g, 28 mmol) in dichloromethane (90 ml) was added followed by diisopropylethylamine (12.3 ml, 71 mmol) dropwise. After 30 minutes the solution was cooled to −78° C. and treated with a solution of 4-benzyloxybenzaldehyde (6.0 g, 28 mmol) in dichloromethane (80 ml). After 2 hours at −78° C., the solution was warmed to 0° C., stirred for 30 minutes and quenched with pH 7 buffer. The layers were separated, the aqueous portion was extracted with dichloromethane, the combined extracts were washed with water and brine, dried over magnesium sulfate and concentrated. The product was isolated by flash chromatography (hexanes/ethyl acetate, 1:1) as an oil (6.5 g).

B.
(S)-4-Benzyl-3-[(1S)-2-(4-benzyloxyphenyl)-1-phenoxyethyl]-2-oxazolidinone Triethylsilane (20 ml, 125 mmol) was added dropwise to a solution of (S)-4-benzyl-3-[(1S),(2R)-2-(4-benzyloxyphenyl)-2-hydroxy-1-phenoxyethyl]-2-oxazolidinone (6.5 g, 12.4 mmol). The solution was stirred for 1 hour then was diluted with ether, washed with water (2×), saturated sodium bicarbonate (2×, carefully), dried over magnesium sulfate and concentrated. The product was isolated by flash chromatography (hexanes/ethyl acetate, 4:1) as an oil (1.8 g).

C.
(S)-4-Benzyl-3-[(1S)-2-(4-hydroxyphenyl)-1-phenoxyethyl]-2-oxazolidinone

A solution of (S)-4-benzyl-3-[(1S)-2-(4-benzyloxyphenyl)-1-phenoxyethyl]-2-oxazolidinone (1.8 g) in ethyl acetate (50 ml) containing 10% palladium on carbon (1.8 g) was hydrogenated at 40 psi overnight. The catalyst was filtered, the solution concentrated and the product purified by flash chromatography (hexanes/ethyl acetate, 3:2) as an oil (0.81 g).

D. (S)-4-Benzyl-3-((1S)-2-[4-(2-phenylethoxy)phenyl]-1-phenoxyethyl}-2-oxazolidinone To a solution of (S)-4-benzyl-3-[(1S)-2-(4-hydroxyphenyl)-1-phenoxyethyl]-2-oxazolidinone (0.25 g, 0.60 mmol), phenethyl alcohol (80 ml, 0.66 mmol) and triphenylphosphine (0.17 g, 0.66 mmol) in tetrahydrofuran (5 ml) was added diisopropylazodicarboxylate (0.13 ml, 0.66 mmol). The mixture was stirred overnight in the dark, then concentrated. The product was isolated by flash chromatography (hexanes/ethyl acetate, 3:1) as a white solid (0.28 g).

E. 2-Phenoxy-3-[4-(2-phenyl)ethoxyphenyl]propanoic acid

A solution of (S)-4-benzyl-3-{(1S)-2-[4-(2-phenylethoxy)phenyl]-1-phenoxyethyl}-2-oxazolidinone (0.28 g, 0.54 mmol) in tetrahydrofuran (10 ml) and 0.5N lithium hydroxide (5 ml) was stirred at 0° C. for 3 hours. The mixture was acidified with 1N HCl, diluted with water and extracted with ethyl acetate (3×). The combined extracts were washed with brine, dried over magnesium sulfate and concentrated. The product was isolated by flash chromatography (hexanes/ethyl acetate/acetic acid, 15:5:1) as a white solid, m.p. 96°–97° C. $[\alpha]_D - 1.0°$ (c 1.76, CHCl$_3$).

The following compounds were prepared by the same sequence from the appropriate starting materials and reagents.

(S)-3-{4-[2-(2-Aminophenyl)]ethoxyphenyl}-2-phenoxypropanoic acid, m p. 100°–103° C. $[\alpha]_D - 9.7°$ (c 1.17, CHCl$_3$).

(S)-3-{4-[2-(4-Benzyloxyphenyl)]ethoxyphenyl}-2phenoxypropanoic acid, m.p. 103°–105° C. $[\alpha]_D + 7.60°$ (c 1.13, CDCl$_3$).

(R)-3-{4-[2-(4-Benzyloxyphenyl)]ethoxyphenyl}-2-phenoxypropanoic acid, m.p. 103°–105° C. $[\alpha]_D - 8.16°$ (c 1.93, CDCl$_3$).

(S)-3-{4-[2-(4-Benzyloxyphenyl)]ethoxyphenyl}-2-ethoxypropanoic acid (oil). $[\alpha]_D + 5.82$ (c 0.55, CDCl$_3$).

EXAMPLE 26

2-Ethoxy-3-(2-benzyl-5-benzoxazolyl)propanoic acid

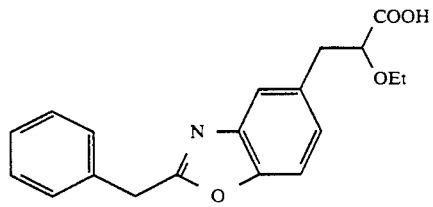

A.
3-(4-Benzyloxy-3-nitrophenyl)-2-ethoxypropanenitrile

This compound was prepared in 3 steps from 4-benzyloxy-3-nitrobenzaldehyde according to the procedure described in Example 18.

B.
3-(3-Amino-4-hydroxyphenyl)-2-ethoxypropanenitrile

A solution of 3-(4-benzyloxy-3-nitrophenyl)-2-ethoxypropanenitrile (0.54 g, 1.7 mmol) in ethanol (25 ml) and acetic acid (75 ml) containing 10% palladium on carbon (0.40 g) was hydrogenated at 45 psi for 1 hour. The catalyst was filtered and the solution concentrated. The residue was treated with 5% sodium bicarbonate (100 ml) and extracted with ethyl acetate (3×100 ml). The combined extracts were washed with water (2×100 ml) and brine (100 ml), dried over sodium sulfate and concentrated. The product was isolated by column chromatography (silica gel, 2% methanol in chloroform) as a solid (0.20 g, m.p. 114°–115° C.)

C.
2-Ethoxy-3-(4-hydroxyphenyl-3-benzamido)propanenitrile

A mixture of 3-(3-amino-4-hydroxyphenyl)-2-ethoxypropanenitrile (0.26 g, 1.2 mmol), phenylacetic acid (0.17 g, 1.2 mmol) and dicyclohexylcarbodiimide (0.25 g, 1.2 mmol) in dimethylformamide (0.5 ml) and tetrahydrofuran (15 ml) was stirred at room temperature for 14 hours. The solution was concentrated, the residue taken up in ethyl acetate (75 ml), this mixture was filtered and the filtrate was washed with water (3×25 ml) and brine (25 ml), dried over sodium sulfate and concentrated. The product was isolated by column chromatography (silica gel, chloroform) as an oil (0.21 g).

D. 2-Ethoxy-3-(2-benzyl-5-benzoxazolyl)propanenitrile

A solution of 2-ethoxy-3-(4-hydroxyphenyl-3-benzamido)propanenitrile (83 mg, 0.26 mmol) and pyridinium p-toluenesulfonate (15 mg, 63 mmol) in xylenes (10 ml) was heated to reflux for 9 hours, then cooled, diluted with ethyl acetate (65 ml), washed with water (3×25 ml) and brine (25 ml), dried over sodium sulfate and concentrated. The product was isolated by column chromatography (silica gel, chloroform) as a yellow oil that solidified on standing (50 mg).

E. 2-Ethoxy-3-(2-benzyl-5-benzoxazolyl)propanoic acid

2-Ethoxy-3-(2-benzyl-5-benzoxazolyl)propanenitrile was hydrolyzed as described in Example 18.
HRMS: Calc. 325.1314;
Found 325.1288.

The following compounds were prepared by the same sequence from the appropriate starting materials and reagents.

3-[2-(4-Benzyloxybenzyl)-5-benzoxazolyl]-2-ethoxypropanoic acid.
HRMS: Calc. 431.1738;
Found 431.1732.

2-Ethoxy-3-[2-(5-methyl-2-phenyl-4-oxazolylmethyl)-5-benzoxazolyl]propanoic acid.
HRMS: Calc. 406.1533;
Found 406.1528.

2-Ethoxy-3-[2-(2-pyridylmethyl)-5-benzoxazolyl]-propanoic acid.
HRMS: Calc. 326.1270;
Found: 326.1266.

EXAMPLE 27
(S),
3,4-Dihydro-2-ethoxy-3-((R)-2-(4-benzyloxybenzyl)-2H-benzopyran-6-yl}propanoic acid

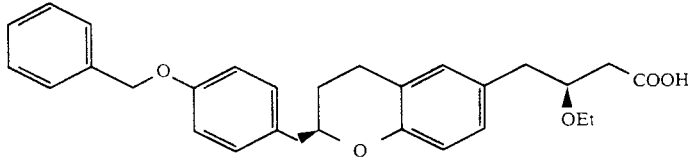

A. (R)-6-{(1R, 2S)-1-Hydroxy-2-ethoxy-3-[(S)-4-benzyl-2-oxo-3-oxazolidinyl]-3-oxopropyl}-2-(4-(benzyloxybenzyl)-2H-benzopyran Trifluoromethanesulfonic acid (11.5 ml, 0.13 mol) was added dropwise to triethylborane (130 ml of a 1N solution in hexanes, 0.13 mol). After the bubbling stopped, the mixture was heated to 40° C. for 1 hour, then cooled to 0° C. A solution of (S)-4-benzyl-3-(ethoxyacetyl)oxazolidin-2-one (Example 19A) (20.6 g, 78 mmol) in dichloromethane (140 ml) was added, followed by diisopropylethylamine (28.5 ml, 0.16 mol, the latter very slowly, so that the temperature does not exceed 5° C. After 20 minutes at 0° C. the solution was cooled to −78° C. and a solution of (R)-2-(4-benzyloxybenzyl)-3,4-dihydro-6-formyl-2H-benzopyran (Example 23 ) (23.4 g, 65 mmol) in dichloromethane (500 ml) was added slowly. The mixture was stirred at −78° C. for 2.5 hours then warmed to 10° C. and quenched with pH 7 buffer (150 ml). The layers were separated, the organic layer was washed with water and brine, dried over magnesium sulfate and concentrated. The product was isolated by flash-chromatography (hexanes/ethyl acetate, 3:2) as an oil (18.8 g).

B. (R)-6-{(S)-2-Ethoxy-3-[(S)-4-benzyl-2-oxo-3-oxazolidinyl]-3-oxopropyl}-2-(4-benzyloxybenzyl)-2H-benzopyran (R)-6-{(1R,2S)-1-Hydroxy-2-ethoxy-3-[(S)-4-benzyl-2-oxo-3-oxazolidinyl]-3-oxopropyl}-2-(4-benzyloxybenzyl)-2H-benzopyran (18.8 g, 31 mmol) was dissolved in trifluoroacetic acid (200 ml) and triethylsilane (49 ml, 0.31 mol) was added. After 45 minutes the volatile components were evaporated and the oily residue was triturated with isopropyl alcohol. The product was purified by flash-chromatography (hexanes/ethyl acetate, 2:1) and obtained as a thick oil (8.9 g).

C. (S)-2-Ethoxy-3-{(2R)-2-(4-benzyloxybenzyl)-3,4-dihydro-2H-benzopyran-6-yl}propanoic acid (R)-6-{(S)-2-Ethoxy-3-[(S)-4-benzyl-2-oxo-3-oxazolidinyl]-3-oxopropyl}-2-(4-benzyloxybenzyl)-2H-benzopyran (8.9 g, 15 mmol) was dissolved in THF (180 ml), cooled to 0° C. and treated with 0.5 N lithium hydroxide (90 ml). The reaction mixture was warmed to room temperature and stirred for 1 hour, then concentrated. The residue was diluted with water and washed with dichloromethane, then acidified with 1N hydrochloric acid, and extracted with ethyl acetate (2×). The combined extracts were washed with brine, dried over magnesium sulfate and concentrated. The product was purified by flash-chromatography (hexanes/ethyl acetate/acetic acid, 12:7:1) and isolated as an oil (6.0 g). The sodium salt was prepared by combining the free acid with sodium methoxide (0.65 g) in methanol and concentrating the solution to dryness. Mp 71°–73° C.

EXAMPLE 28
(S)-3,4-Dihydro-2-ethoxy-3-{(R)-2-(4-benzyloxybenzyl)-2H-benzopyran-6-yl}propanoic acid (S)-3,4-Dihydro-2-ethoxy-3-{(R)-2-(4-benzyloxybenzyl)-2H-benzopyran-6-yl}propanoic acid was prepared by substantially the same sequence recited in Example 27 but substituting (R)-2-benzyl-6-formylbenzopyran (Example 24) for (R)-2-(4-benzyloxybenzyl)-3,4-dihydro-6-formyl-2H-benzopyran.

I claim:
1. A compound of the formula

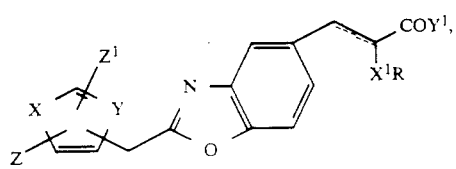

wherein:

---- represents a bond or no bond;

R is $C_1$ to $C_8$ alkyl, $C_3$ to $C_7$ cycloalkyl, $C_3$ to $C_8$ alkenyl, $C_3$ to $C_8$ alkynyl, phenyl, $C_7$ to $C_8$ phenylalkyl, $C_2$ to $C_8$ alkanoyl, or one of said groups mono- or disubstituted with $C_1$ to $C_3$ alkyl, trifluoromethyl, hydroxy, $C_1$ to $C_3$ alkoxy, fluoro or chloro;

X is S, $NR^2$, —CH=CH—;

$R^2$ is hydrogen, $C_1$ to $C_3$ alkyl, phenyl or benzyl;

Y is CH;

Z is hydrogen, $C_1$ to $C_7$ alkyl, $C_3$ to $C_7$ cycloalkyl, phenyl or phenyl mono- or disubstituted with $C_1$ to $C_3$ alkyl, trifluoromethyl, $C_1$ to $C_3$ alkoxy, phenyl, phenoxy, benzyl, benzoloxy, fluoro or chloro;

$X^1$ is O, S, SO or $SO_2$;

$Y^1$ is hydroxy, $C_1$ to $C_3$ alkoxy, phenoxy, benzyloxy, amino, $C_1$ to $C_4$ alkanoylamino, $C_1$ to $C_4$ alkanesulfonylamino, benzenesulfonylamino, naphthalenesulfonylamino, di ($C_1$ to $C_3$ alkyl)aminosulfonylamino, or one of said groups mono- or disubstituted with $C_1$ to $C_3$ alkyl, trifluoromethyl, hydroxy, $C_1$ to $C_3$ alkoxy, fluoro or chloro; and $Z^1$ is hydrogen or $C_1$ to $C_3$ alkyl;

a pharmaceutically acceptable cationic acid addition salt thereof when $Y^1$ is hydroxy; or a pharmaceutically acceptable acid addition salt thereof when the compound contains a basic nitrogen atom.

2. A compound according to claim 1 wherein:

---- represents no bond;

X is —CH=CH—;

Y is —CH—;

$Z^1$ is hydrogen;

$X^1$ is O; and $Y^1$ is hydroxy.

3. A compound according to claim 2 wherein:

Z is hydrogen, benzyloxy or m-fluorobenzyloxy; and

R is $C_1$ to $C_4$ alkyl, phenyl or benzyl.

4. A pharmaceutical composition for use in a hyperglycemic mammal which comprises a blood glucose lowering effective amount of a compound according to claim 1.

* * * * *